US009012183B2

(12) United States Patent  (10) Patent No.: US 9,012,183 B2
Lambowitz et al.  (45) Date of Patent: Apr. 21, 2015

(54) USE OF TEMPLATE SWITCHING FOR DNA SYNTHESIS

(75) Inventors: Alan M. Lambowitz, Austin, TX (US); Sabine Mohr, Austin, TX (US); Travis B. White, Austin, TX (US); Scott Kuersten, Fitchburg, WI (US)

(73) Assignee: Board of Regents, The University of Texas System, Austin, TX (US)

( * ) Notice: Subject to any disclaimer, the term of this patent is extended or adjusted under 35 U.S.C. 154(b) by 81 days.

(21) Appl. No.: 14/000,513

(22) PCT Filed: Feb. 23, 2012

(86) PCT No.: PCT/US2012/026263
§ 371 (c)(1),
(2), (4) Date: Aug. 20, 2013

(87) PCT Pub. No.: WO2012/116146
PCT Pub. Date: Aug. 30, 2012

(65) Prior Publication Data
US 2014/0004569 A1    Jan. 2, 2014

Related U.S. Application Data

(60) Provisional application No. 61/445,761, filed on Feb. 23, 2011.

(51) Int. Cl.
*C12P 19/34* (2006.01)
*C12N 15/10* (2006.01)
*C12Q 1/68* (2006.01)

(52) U.S. Cl.
CPC ............. *C12P 19/34* (2013.01); *C12N 15/1096* (2013.01); *C12Q 1/6806* (2013.01)

(58) Field of Classification Search
None
See application file for complete search history.

(56) References Cited

U.S. PATENT DOCUMENTS

| | | |
|---|---|---|
| 2004/0171041 A1 | 9/2004 | Dahl et al. |
| 2006/0281079 A1 | 12/2006 | Eickbush et al. |
| 2008/0182239 A1 | 7/2008 | Mullinax et al. |
| 2011/0020897 A1 | 1/2011 | Lampson et al. |
| 2012/0009630 A1 | 1/2012 | Lambowitz et al. |

OTHER PUBLICATIONS

International Search Report from corresponding Int'l. Patent Appl. No. PCT/US2012/026263, 2 pages, May 20, 2012.
Bibillo & Eickbush "The Reverse Transcriptase of the R2 Non-LTR Retrotransposon: Continuous Synthesis of cDNA on Non-continuous RNA Templates" 2002 J. Mol. Biol. vol. 316, pp. 459-473.
Blocker, Mohr, Conlan, Qi, Belfort & Lambowitz "Domain Structure and Three-Dimensional Model of a Group II Intron-Encoded Reverse Transcriptase" 2005 RNA vol. 11, pp. 14-28.
Candales, Duong, Hood, Li, Neufeld, Sun, McNeil, Wu, Jarding & Zimmerly "Databasde for Bacterial Group II Introns" 2011, Nucleic Acids Research, vol. 40, pp. 187-190.
Chen & Lambowitz, "De Novo and DNA Primer-Mediated Initiation of cDNA Synthesis by the Mauriceville Retroplasmid Reverse Trasncriptase Involve Recognition of a 3' CCA Sequence" 1997, J. Mol. Biol., vol. 271, pp. 311-332.
Clark, "Novel Non-Templated Nucleotide Addition Reactions Catalyzed by Procaryotic and Eucaryotic DNA Polymerases" 1988 Nucleic Acids Research, vol. 16, No. 20, pp. 9677-9686.
Clark, Joyce & Beardsley, "Novel Blunt-End Addition Reactions Catalyzed by DNA Polymerase I of *Escherichia coli*", 1987, J. Mol. Biol. vol. 198, pp. 123-127.
Dai, Toor, Olson, Keeping & Zimmerly, "Database for Mobile Group II Introns" 2003, Nucleic Acids Research, vol. 31, No. 1, pp. 424-426.
Golinelli & Hughes, "Nontemplated Base Addition by HIB-1 RT can Induce Nonspecific Strand Transfer In Vitro" 2002, Virology, vol. 294, pp. 122-134.
Granneman, Kudla, Petfalski & Tollervey, "Identification of Protein Binding Sites on U3 snoRNA and pre-rRNA buy UV cross-linking and High-Throughput Analysis of cDNAs" 2006, PNAS, vol. 106, No. 24, pp. 9613-9618.
Hu, "DNA Polymerase-Catalyzed Addition of Nontemplated Extra Nucleotides to the 3' End of a DNA Fragment" 1993, DNA Cell Biol., vol. 12, pp. 763-770.
Ingolia, Ghaemmaghami, Newman & Weissman "Genome-Wide Analysis in Vivo of Translation with Nucleotide Resolution Using Ribsome Profiling" 2009, Science, vol. 324, pp. 218-223.
Konig, Zarnack, Rot, Curk, Kayikci, Zupan, Turner, Luscombe & Ule, "iCLIP Reveals the Function of hnRNP Paricles in Splicing at Individual Nucleotide Resolution" 2011, Nat. Struct. Mol. Biol. vol. 17 No. 7, 16 pages.
Lambowitz & Zimmerly, "Group II Introns: Mobile Ribozymes that Invade DNA" 2011, Cold Spring Harbor Laboratory Press, 19 pages.
Lamm, Stadler, Zhang, Gent, & Fire, "Multimodal RNA-seq using Single-Strand, Double-Strand, and CircLigase-Based Capture Yields a Refined and Extended Description of the *C. elegans* Transcriptome" 2011, Cold Spring Harbor Laboratory Press, pp. 265-275.
Lau, Lim, Winstein & Bartel "An Abundant Class of Tiny RNAs with Probable Regulatory Roles in *Caenorhabditis elegans*" 2001, Science, vol. 294, pp. 858-862.

(Continued)

*Primary Examiner* — James Martinell
(74) *Attorney, Agent, or Firm* — Tarolli, Sundheim, Covell & Tummino LLP

(57) ABSTRACT

A method of preparing a DNA copy of a target polynucleotide using template switching is described. The method includes mixing a double stranded template/primer substrate made up of a DNA primer oligonucleotide associated with a complementary oligonucleotide template strand with a target polynucleotide in a reaction medium and adding a suitable amount of a non-retroviral reverse transcriptase to the reaction medium to extend the DNA primer oligonucleotide from its 3' end to provide a DNA copy polynucleotide. The DNA copy polynucleotide includes a complementary target DNA polynucleotide that is synthesized using the target polynucleotide as a template. Methods of adding nucleotides to the double stranded template/primer substrate are also described. The method can be used to facilitate detection, PCR amplification, cloning, and determination of RNA and DNA sequences.

33 Claims, 16 Drawing Sheets

(56) References Cited

OTHER PUBLICATIONS

Levin, Yassour, Adiconis, Nusbaum, Thompson, Friedman, Gnirke & Regev, "Comprehensive Comparative Analysis of Strand-Specific RNA Sequencing Methods" 2010, Nat. Methods., vol. 7, No. 9, pp. 709-715.

Linsen, Wit, Jenssens, Heater, Chapman, Prkin, Fritz,, Wyman, Bruijn, Voest, Kuersten, Tewari & Cuppen, "Limitations and Possibilities of Small RNA Digital Gene Expression Profiling" 2009, Nature Methods, vol. 6, No. 7, pp. 474-476.

Magnuson, Ally, Nylund, Karanjawala, Rayman, Knapp, Lowe, Ghosh & Collins, "Substrate Nucleotide-Determined Non-Templated Addition of Adenine by Taq DNA Polymerase: Implications for PCR-Based Genotyping and Cloning" 1996 Biotechinques vol. 21, No. 4, pp. 700-709.

Moretz & Lampson "A Group IIC-Type Intron Interrupts the rRNA Methylase Gene of *Geobacillus stearothermophilus* Strain 10" 2010, Journal of Bacteriology, vol. 192, No. 19, pp. 5245-5248.

Oz-Gleenberg, Herschhorn & Hizi, "Reverse Transcriptases can Clamp Together Nucleic Acids Strands with Two Complementary Bases at Their 3'-Termini for Initiating DNA Synthesis" 2011, Nucleic Acids Research, vol. 39, No. 3, pp. 1042-1053.

Patel & Preson "Marked Infidelity of Human Immunodeficiency Virus Type 1 Reverse Transcriptase at RNA and DNA Template Ends" 1994, Proc. Natl. Acad. Sci., vol. 91, pp. 549-553.

Peliska & Benkovic, "Mechanism of DNA Strand Transfer Reactions Catalyzed by HIV-1 Reverse Transcriptase" 1992, Science, vol. 258, No. 5805, pp. 1112-1118.

Saldanha, Chen, Wank, Matsuura, Edwards, & Lambowitz "RNA and Protein Catalysis in Group II Intron Splicing and Mobility Reactions Using Purified Components" 1999, Biochemistry, vol. 38, pp. 9069-9083.

Smith, Zhong, Matsuura, Lambowitz & Belfort, "Recruitment of Host Functions Suggests a Repair Pathway for Late Steps in Group II Intron Retrohoming" 2005, Cold Spring Harbor Laboratory Press, pp. 2477-2487.

Vellore, Moretz & Lampson, "A Group II Intron-Type Open Reading Frame from the Thermophile *Bacillus* (*Geobacillus*) *stearothermophilus* Encodes a Heat-Stable Reverse Transcriptase" 2004, Applied and Environmental Microbiology, vol. 70, No. 12, pp. 7140-7147.

Xiong & Eickbush, "Origin and Evolution of Retroelements Based Upon their Reverse Transcriptase Sequences" 1990. The EMBO Journal, vol. 9, No. 10, pp. 3353-3352.

Zhong & Lambowitz, "Group II Intron Mobility Using Nascent Strands at DNA Replication Forks to Prime Reverse Transcription" 2003, The EMBO Journal, vol. 22, No. 17, pp. 4555-4565.

Zhu, Machleder, Chenchik, Li & Siebert, "Reverse Transcriptase Template Switching: A SMART Approach for Full-Length cDNA Library Construction" 2001, BioTechniques, vol. 30, No. 4, pp. 892-897.

Bibillo and Eickbush, "End-to-End Template Jumping by the Reverse Transcriptase Encoded by the R2 Retrotransposon" The Journal of Biological Chemistry, vol. 279, No. 15, Apr. 2004, pp. 14945-14953.

Fig. 2
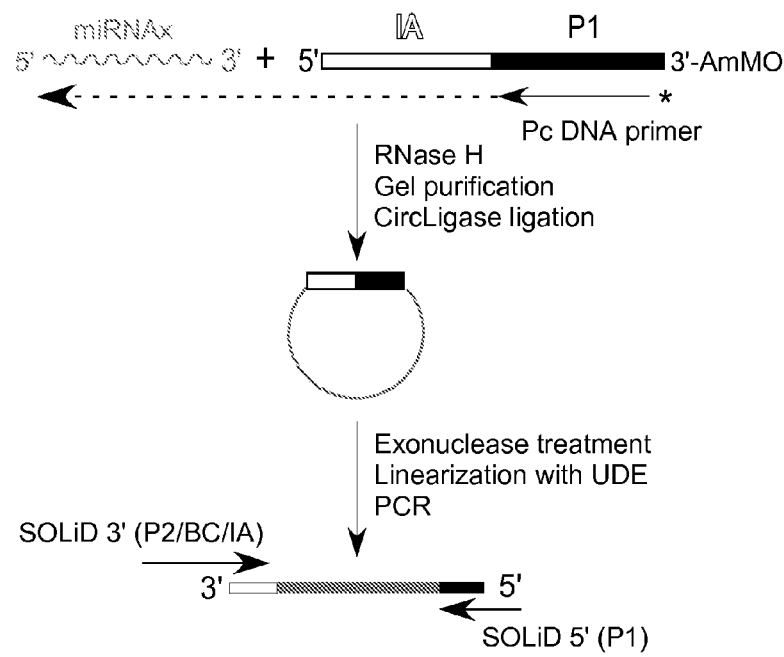
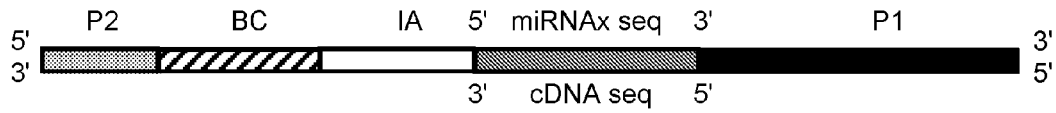
IA-P1 RNA/Pc DNA template/primer
```
         IA                    P1
5' CGCCUUGGCCGUACAGCAGCCUCUCUAUGGGCAGUCGGUGAU 3'-AmMO
              3' ATGTCGUCGGAGAGATACCCGTCAGCCACTA 5'
                            Pc DNA primer
```
SOLiD 5' Primer (P1)
5' CCACTACGCCTCCGCTTTCCTCTCTATGGGCAGTCGGTGAT 3'
SOLiD 3' Primer with barcode (X's; P2/BC/IA)
5' CTGCCCCGGGTTCCTCATTCTCTXXXXXXXXXXCTGCTGTACGGCCAAGGCG 3'
         P2              BC                IA

Fig.3

```
                              miRNAx                          IA-P1 RNA
        RNA       5'NNCGCUUCAGAGAGAAAUCNN 3'   5'CGCCUUGGCCGUACA..GUGAU 3'-AmMO
        cDNA      3'NNGCGAAGTCTCTCTTTAGNN 5'              3'ATGT..CACTA 5'
                                                              Pc DNA primer
                         cDNA            IA-P1
                   GAAGTCTCTCTTTA    GCGGAA.. 5'
                   GAAGTCTCTCTTTAGTAGCGGAA..
              TCGCGAAGTCTCgaTcGTCGGGCGGAA..
              TCGCGAAGTCTCTCTTTAGCCGCGGAA..
              TCGCGAAGTCTCTCTTTAGAAGCGGAA..
             aCCGCGAAGTCTCTCTTTAGGCGCGGAA..
             aCGGCGAAGTCTCTCTTTAGTAGCGGAA..
             gGTGCGAAGTCTCTCTTTAGCGGCGGAA..
             aGGattgtGTCTCTCTTTAGTAGCGGAA..
             aACGGCGAAGTCTCTCTTTAGCCGCGGAA..
            agTGGCGAAGTCTCTCTTTAGTAGCGGAA..
            agTNGCGAAGTCTCTCTTTAGGAGCGGAA..
            agTCGCGAAGTCTCTCTTTAGTAGCGGAA..
            aaCAGCGAAGTCTCTCTTTAGGCGCGGAA..
            aaCAGCGAAGTCTCTCTTTAGGCGCGGAA..
            agGTGCGAAGTCTCTCTTTAGTGGCGGAA..
            caGAGCGAAGTCTaTCTTTAGCAGCGGAA..
            aaCCGCGAAGTCTCTCTTTAGAGGCGGAA..
           gaaCCGCGAAGTCTCTCTTTAGTCGCGGAA..
           gaaCTGCGAAGTCTCTCTTTAGAAGCGGAA..
           agaCCGCGAAGTCTCTCTTTAGGCGCGGAA..
         taggaCCGCGAAGTCTCTCTTTAGTAGCGGAA..
     aaactccccaaACGCGAANTNNNTNTTTAGTGGCGGAA..
     actcccccccaaCCGCGAAGTCTCTCTTTAGTCGCGGAA..
gtacttgcaggacgaCCGCGAAGTCTCTCTTTAGCAGCGGAA..
```

Fig. 4B

|  |  | -40 Exon 1 DNA -1 | 1 Ll.LtrB 60 | Freq. |
|---|---|---|---|---|
|  |  | 5' TGTG...TAAC | GUGCGCCCAGAUAGG- 45 nt 3' |  |
|  |  | 3' ACAC...ATTG | CACGCGGGTCTATCC ◄─── * 5' |  |
|  |  | DNA product | cDNA      Primer c DNA |  |
|  | Band a |  | 3'-ACGCGGGTCTATCC────* 5' | 1 |
|  |  |  | 3'CACGCGGGTCTATCC────* 5' | 9 |
|  | Band b | 3'aa | CACGCGGGTCTATCC────* 5' | 2 |
|  |  | 3'aaa | CACGCGGGTCTATCC────* 5' | 3 |
| Band c | 3'aaa ACAC...ATTG |  | ─────────CC────* 5' | 1 |
| Band d | 3' | -30    -1<br>TaG...ATTG   aa | CACGCGGGTCTATCC────* 5' | 1 |
|  | 3'a | -35    -1<br>AAC...ATTG | CACGCGGGTCTATCC────* 5' | 1 |
| Band e | 3'   ACAC...ATTG |  | CACGCGGGTCTATCC────* 5' | 1 |
|  | 3'a  ACAC...ATTG |  | CACGCGGGTCTATCC────* 5' | 1 |
|  | 3'c  ACAC...ATTG |  | CACGCGGGTCTATCC────* 5' | 1 |
|  | 3'aa ACAC...ATTG |  | CACGCGGGTCTATCC────* 5' | 1 |
|  | 3'a  ACAC...ATTG | a | CACGCGGGTCTATCC────* 5' | 1 |
|  | 3'aaa ACAC...ATTG | a | CACGCGGGTCTATCC────* 5' | 2 |
|  | 3'aa ACAC...ATTG | aa | CACGCGGGTCTATCC────* 5' | 2 |
|  | 3'aaaa ACAC...ATTG |  | CACGCGGGTCTATCC────* 5' | 1 |
|  | 3'aaa ACAC...ATTG |  | CACGCGGGTCTATCC────* 5'<br>     ĉ | 2 |

Fig. 4C

|  |  | -40 Exon 1 RNA -1 | 1 LI.LtrB 60 | Freq. |
|---|---|---|---|---|
|  |  | 5' UGUG...UAAC | GUGCGCCCAGAUAGG— 45 nt 3' |  |
|  |  | 3' ACAC...ATTG | CACGCGGGTCTATCC◄——*5' |  |
|  |  | cDNA | cDNA    Primer cDNA |  |

| Band h | | | 3'CACGCGGGTCTATCC———*5' | 9 |
|---|---|---|---|---|
| | | | 3'CACGCGGGTCTATCt———*5' | 1 |

| Band i | | 3'aa | CACGCGGGTCTATCC———*5' | 3 |
|---|---|---|---|---|
| | | 3'ta | CACGCGGGTCTATCC———*5' | 1 |
| | | 3'aaa | CACGCGGGTCTATCC———*5' | 6 |
| | | 3'aga | CACGCGGGTCTATCC———*5' | 1 |
| | | 3'aaaa | CACtCGGGTCTATCC———*5' | 1 |

| Band j | 3'a | -17       -1<br>CAC...ATTG | aa CACGCGGGTCTATCC———*5' | 1 |
|---|---|---|---|---|
| | 3' | -26       -1<br>TGC...ATTG | CACGCGGGTCTATCC———*5' | 2 |
| | 3' | -26       -2<br>TGC...ATT | a  CACGCGGGTCTATCC———*5' | 3 |
| | 3' | -26       -1<br>TGC...ATTG | a  CACGCGGGTCTATCC———*5' | 2 |
| | 3' | -26       -2<br>TGC...ATT | ag CACGCGGGTCTATCC———*5' | 1 |
| | 3' | -30       -2<br>TGG...ATT | c  CACGCGGGTCTATCC———*5' | 1 |

| Band k | 3'a | -36       -2<br>TAA...ATT | CACGCGGGTCTATCC———*5' | 1 |
|---|---|---|---|---|
| | 3'ta | -35       -2<br>AaC...ATT | CACGCGGGTCTATCC———*5' | 1 |
| | 3'ta | -40       -2<br>ACAC...ATT | CACGCGGGTCTATCC———*5' | 1 |

| Band l | 3'gaa | -40       -2<br>ACAC...ATT | a  CACGCGGGTCTATCC———*5' | 1 |
|---|---|---|---|---|
| | 3'aa | ACAC...ATTG | aa CACGCGaGTCTATCC———*5' | 1 |

Fig. 5B

```
                                                    Exon 2
                                            5'[CATATCATT- 30 nt ]3'    Frequency
                                            3'[GTATAGTAAA]◄────*5'
                                              cDNA     Primer e2 DNA Band a              3'GTATAGTAAA5'                  7

Band b   3'accc     GTATAGTAAA5'                    1
                               3'aaaccc   GTATAGTAAA5'                    3
                               3'aacccc   GTATAGTAAA5'                    1
                               3'aagccc   GTATAGTAAA5'                    1
                               3'aaaaccc  GTATAGTAAA5'                    1
                               3'aaccccc  GTATAGTAAA5'                    1
                               3'ccccccc  GTATAGTAAA5'                    1
                               3'aagcccc  GTATAGTAAA5'                    1
                               3'accc     GTATAGTAAA5'                    1
                                                   ^
                                                   a
                               3'gccc     GTATAGTAAA5'                    1
                                                   ^
                                                   a
                         1  Exon 2  40           Exon 2
                      5'[CAUA...AAAC]   [CAUAUCAUUU- 30 nt ]3'
                      3'[GTAT...TTTG]   [GTATAGTAAA]◄────*5'
                         cDNA             cDNA    Primer e2

Band c     3'aaaccc GTAT...TTTG ggccc GTATAGTAAA5'                2
                    3'aagccc GTAT...TTTG gcccc GTATAGTAAA5'                1

1  Exon 2  40       1  Exon 2  40         Exon 2
        5'[CAUA...AAAC]      [CAUA...AAAC]      [CAUAUCAUUU- 30 nt ]3'
        3'[GTAT...TTTG]      [GTAT...TTTG]      [GTATAGTAAA]◄────*5'
           cDNA                cDNA               cDNA    Primer e2
Band d
3'aaccc   GTAT...TTTG ggccc    GTAT...TTTG gggccc    GTATAGTAAA5'          1
3'gccc    GTAT...TTTG gggccc   GTAT...TTTG gggaccc   GTATAGTAAA5'          1
3'gacccc  GTAT...TTTG gtccccc  GTAT...TTTG cccccc    GTATAGTAAA5'          1
3'accc    GTAT...TTTG gaccc    GTAT...TTTG ggggagccc GTATAGTAAA5'          1
3'accc    GTAT...TTTG gtcaccc  GTAT...TTTG ggtcccc   GTATAGTAAA5'          1
3'accc    GTAT...TTTG gggaccc  GTAT...TTTG gtcacccc  GTATAGTAAA5'          1
3'aaaaccc GTAT...TTTG ggaccccc GTAT...TTTG gcccc     GTATAGTAAA5'          1
3'taaccc  GTAT...TTTG ggtccc   GTAT...TTTG ggggaccc  GTATAGTAAA5'          1
3'aaaaccc GTAT...TTTG gaccccc  GTAT...TTTG ggtcccc   GTATAGTAAA5'          1
          1       40           1      34
3'gccc    GTAT...TTTG gccc     GTAT...GAC  gcaaaccc  GTATAGTAAA5'          1
```

Fig. 7

```
                miRNAx                            IA-P1 RNA

5'NNCGCUUCAGAGAGAAAUCNN 3'    5'CGCCUUGGCCGUACA..GUGAU 3'AmMO
3'NNGCGAAGTCTCTCTTTAGNN 5'       3'   ATGT..CACTA 5'
                                       Pc DNA primer Reads
     TCGCGAAGTCTCTCTTTAGGA    11794
     TCGCGAAGTCTCTCTTTAGCA    10235
     CCGCGAAGTCTCTCTTTAGGA     7929
     TCGCGAAGTCTCTCTTTAGAA     6468
     CCGCGAAGTCTCTCTTTAGCA     6134
     TCGCGAAGTCTCTCTTTAGTA     6111
     ACGCGAAGTCTCTCTTTAGGA     5795
     TAGCGAAGTCTCTCTTTAGCA     5040
     ATGCGAAGTCTCTCTTTAGCA     4884
     TTGCGAAGTCTCTCTTTAGCA     4831
     CCGCGAAGTCTCTCTTTAGTA     4682
     CTGCGAAGTCTCTCTTTAGGA     3943
     TTGCGAAGTCTCTCTTTAGGA     3928
     ACGCGAAGTCTCTCTTTAGTA     3632
     CAGCGAAGTCTCTCTTTAGGA     3546
    aCCGCGAAGTCTCTCTTTAGGA     5213
    aCCGCGAAGTCTCTCTTTAGCA     4788
    aCCGCGAAGTCTCTCTTTAGTA     4590
    aCAGCGAAGTCTCTCTTTAGTA     4272
    aCAGCGAAGTCTCTCTTTAGGA     3457
```

USE OF TEMPLATE SWITCHING FOR DNA SYNTHESIS

CONTINUING APPLICATION DATA

This application claims the benefit of U.S. Provisional Application Ser. No. 61/445,761, filed Feb. 23, 2011, which is incorporated by reference herein.

GOVERNMENT FUNDING

This invention was made with government support under Grant Nos. R01 GM037949 and R01 GM037951 awarded by the National Institutes of Health. The United States government has certain rights in this invention.

SEQUENCE LISTING

The instant application contains a Sequence Listing which has been submitted in ASCII format via EFS-Web and is hereby incorporated by reference in its entirety. Said ASCII copy, created on Feb. 23, 2012, is named 31594024.txt and is 34,166 bytes in size.

BACKGROUND OF THE INVENTION

Reverse transcriptases (RTs) are employed in biotechnology to synthesize cDNA copies of RNAs for a variety of applications, including RT-PCR and qRT-PCR, construction of cDNA libraries, generation of probes for microarrays, and conventional and next-generation RNA sequencing. The synthesis of cDNAs corresponding to long polyadenylated RNAs can be accomplished by using random hexamer primers or an oligo(dT)-containing primer, which is complementary to the poly(A) tail. However, the strand-specific cloning and sequencing of cDNAs corresponding to non-polyadenylated RNAs, such as miRNAs or protein-bound RNA fragments, typically requires ligating DNA, RNA or chimeric RNA/DNA oligonucleotide adaptors containing PCR-primer-binding sites to the termini of the RNA or cDNA strand (Lau et al. 2001; Levin et al. 2010; Lamm et al. 2011). The adaptors are commonly ligated to the RNA template using RNA ligases, either sequentially to the 3' and 5' ends of the RNA (e.g., Roch 454 Life Sciences® sequencing and Illumina® next-generation sequencing) or simultaneously to both RNA ends (e.g., SOLiD™ next-generation sequencing) (Linsen et al. 2009). For some applications, the first adaptor is ligated to the 3' end of the RNA for reverse transcription and the second adaptor to the 3' end of the resulting cDNA (e.g., cross-linking and analysis of cDNAs (CRAC) of protein-bound RNA fragments; Granneman et al. 2009). In one variation, the ligation of a second adaptor is circumvented by using a non-templated nucleotide addition reaction of the reverse transcriptase to add C-residues to the 3' end of the cDNA, enabling annealing of a second adaptor containing complementary G-residues for second-strand synthesis (Zhu et al. 2001). In another variation, the ligation of a second adaptor is circumvented by circularization of the cDNA followed by linearization and PCR amplification using bidirectional primer binding sites in the first adaptor, for example in individual-nucleotide resolution UV-crosslinking and immunoprecipitation (iCLIP, König et al. 2010) or genome-wide in vivo analysis of translation with nucleotide resolution using ribosome profiling (Ingolia et al. 2009).

Unfortunately, although the attachment of oligonucleotide adaptors is needed for facile PCR amplification for the cloning and sequencing of cDNAs corresponding to non-polyadenylated RNAs and RNA fragments, the use of ligases to attach adaptors is a time-consuming, expensive, and inefficient step. Moreover, RNA ligases commonly used for adaptor ligation have distinct nucleotide preferences for the ends being ligated, leading to biased representation of cDNAs in the constructed libraries (Linsen et al. 2009; Levin et al. 2010).

Retroelements, genetic elements that encode RTs, are divided into two major families denoted LTR-containing retroelements and non-LTR-containing retroelements (Xiong and Eickbush 1990). Retroviruses, whose RTs are commonly used in biotechnology, are well-known examples of LTR-containing retroelements. Non-LTR-retroelements are a diverse family of RT-encoding elements that includes retroplasmids, non-LTR-retrotransposons, retrons, and mobile group II introns (Xiong and Eickbush 1990). Mobile group II introns consist of a catalytically active intron RNA ("ribozyme") and an intron-encoded RT, which function together to promote RNA splicing and intron mobility (Lambowitz and Zimmerly 2010). Group II intron RTs typically consist of four conserved domains: RT, which contains seven conserved sequence blocks (RT1-7) found in the fingers and palm regions of retroviral RTs; X, a region required for RNA splicing activity corresponding at least in part to the thumb domain of retroviral RTs; D, a DNA-binding domain involved in DNA target site recognition; and En, a DNA endonuclease domain that cleaves the DNA target site to generate the primer for reverse transcription (Blocker et al. 2005; Lambowitz and Zimmerly 2010). The En domain is missing in some group II intron RTs, which instead use nascent strands at DNA replication forks to prime reverse transcription (Zhong and Lambowitz 2003; Lambowitz and Zimmerly 2010). The RT and X/thumb domains of group II intron RTs are larger than those of retroviral RTs due to an N-terminal extension, an additional N-terminal conserved sequence block (RT-0), and insertions between the conserved sequence blocks in the RT and X/thumb domain (Lambowitz and Zimmerly 2010). RT-0 and some of the insertions between conserved sequence blocks in the RT domain are also found in other non-LTR-retroelement RTs (Blocker et al. 2005). Unlike retroviral RTs, group II intron and non-LTR-retroelement RTs lack an RNase H domain.

The RTs encoded by retroplasmids and non-LTR-retrotransposons have been found to differ from retroviral RTs in being able to template switch directly from an initial RNA template to the 3' end of a new RNA template that has little or no complementarity to the 3' end of the cDNA synthesized from the initial template (Chen and Lambowitz 1997; Bibillo and Eickbush 2002, 2004; Kennell et al. 1994).

SUMMARY OF THE INVENTION

As disclosed herein the reverse transcriptases (RTs) encoded by certain classes of retroelements, most notably mobile group II introns, provide solutions for the difficulties associated with adaptor ligation, and more generally, provide new methods that facilitate detection, PCR amplification, and cloning of RNA and DNA sequences. The inventors hypothesized that non-retroviral RTs might be capable of template switching with little or no complementarity between the cDNA synthesized from the initial template and the 3' end of the new RNA or DNA template, and that this reaction might be used to synthesize a continuous cDNA that directly links an adaptor sequence to a target RNA or DNA sequence without ligation. The composite cDNA could then be ligated to a second adaptor molecule at the 3' end of the cDNA or circularized, for example with CircLigase, an enzyme that efficiently circularizes single-stranded DNA (Polidoros et al.

2006), allowing PCR amplification with bidirectional primers that anneal to different portions of the first adaptor. For some applications, such primers could add barcodes for next-generation/deep sequencing.

Use of a non-retroviral reverse transcriptase (RT) to synthesize cDNAs in which a target polynucleotide strand or strands containing sequences of interest are linked by template switching from one or more adaptor sequences and/or non-templated nucleotide residues that are added to the 3' end of the cDNA is described. The adaptor sequence may contain PCR primer-binding sites, whose attachment facilitates subsequent detection, PCR amplification, cDNA library construction, and sequencing of RNA or DNA molecules. The adaptor sequence may also contain other useful sequences, such as an affinity tag sequence for the subsequent purification of cDNAs. Non-templated nucleotide addition to the 3' end of cDNAs may facilitate their subsequent amplification and cloning, e.g., by enabling the annealing of PCR primers containing nucleotide residues complementary to those added by non-templated nucleotide addition, or by enabling cloning of the cDNAs into vectors containing nucleotide residues complementary to those added by non-templated nucleotide addition. Methods for directing template switching by reverse transcriptases to target polynucleotide sequences having specific 3'-terminal nucleotide residues and for minimizing biases in template switching by reverse transcriptases among polynucleotide strands having different 3'-terminal nucleotide residues are also described. The present disclosure also provides methods for template switching by reverse transcriptases from RNA to DNA templates or between DNA templates, enabling linkage of different DNA and RNA sequences. For example, the ability of a reverse transcriptase to template jump between DNA templates could be used to attach adaptors to single-stranded DNAs for second-strand synthesis or for making DNA libraries from single-stranded genomic DNA. Methods for using non-retroviral RTs to add non-templated nucleotide residues to other DNAs that are not synthesized by the RT to facilitate their detection, PCR amplification, cloning, and sequencing are also described. The present disclosure also provides methods for decreasing non-templated nucleotide addition by non-retroviral RTs for applications in which such non-templated nucleotide addition would be deleterious—e.g., determination of accurate cDNA length by capillary electrophoresis, RNA structure mapping, and RNA footprinting.

It is to be understood that both the foregoing general description and the following detailed description are exemplary and explanatory only and are not restrictive of the invention, as claimed.

BRIEF DESCRIPTION OF THE FIGURES

FIG. 2. Method for cDNA cloning via group II intron RT template-switching and circularization with CircLigase. In the first step, the group II intron RT template switches from the IA-P1 RNA/Pc DNA template/primer to miRNAx to generate a continuous cDNA that links the IA-P1 adaptor sequence to that of miRNAx. The products are incubated with RNase H to digest the RNA templates, gel-purified, and circularized with CircLigase I or II. After digestion of unincorporated primers with exonuclease I, the cDNA products are re-linearized with uracil-DNA excision mix (UDE; Epicentre®) at a deoxyuridine (underlined U in the Pc DNA primer sequence) that had been incorporated into the primer and then amplified by PCR with primers that introduce additional adaptor sequences and barcodes for next generation sequencing. The sequences (SEQ ID NOS 5, 24 and 8-10, respectively, in order of appearance) of the IA-P1 RNA/Pc DNA template-primer substrate and the PCR primers for the SOLiD sequencing are shown at the bottom. The IA-P1 RNA has a 3' aminomodifier (denoted AmMO) to impede template switching to that RNA end. X's denote barcode (BC) nucleotide residues, and * denotes $^{32}$P-label at the 5' end of the primer.

FIG. 3. Cloning and sequencing of cDNAs (SEQ ID NO: 28) corresponding to a miRNA (SEQ ID NO: 26) in which the two 5'- and two 3'-nucleotide residues were randomized. cDNAs were synthesized via TeI4c-MRF RT template-switching from the IA-P 1 RNA/Pc DNA template/primer substrate ("IA-P1 RNA" sequence disclosed as SEQ ID NO: 27) to miRNAx for 15 min. under reaction conditions used for that enzyme in FIG. 1, gel-purified, circularized with CircLigase II, PCR amplified using Flash Phusion® polymerase with the SOLID 5' and 3' primers, TA cloned into PCR2.1 TOPO (Invitrogen™), and Sanger sequenced with the M13 (−20)F primer. The randomized nucleotide positions at the 5'- and 3'-ends of miRNA are underlined and highlighted with gray shading, respectively. In the product sequences (SEQ ID NOS 29-53, respectively, in order of appearance), mutant nucleotide residues are shown in lower-case letters, and non-templated nucleotide residues are shown in bold lower-case letters. N in product sequences denotes nucleotides that could not be identified unambiguously in the sequence.

(3) and (4) LtrA incubated with $^{32}$P-labeled Pri c and E1 DNA or RNA, respectively; (5) and (6) LtrA incubated with L1.LtrB RNA/$^{32}$P-labeled Pri c template/primer substrate and E1 DNA or RNA, respectively. In the schematics, the L1.LtrB RT is shown as a gray oval, and the direction of DNA synthesis is indicated by a dotted arrow within the gray oval. Bands excised for DNA sequencing (a-n) are indicated in the gel. The numbers to the right of the gel indicate the nucleotide position of the 5'-$^{32}$P-labeled 10-bp ladder (Invitrogen™). (B) and (C) Sequences of DNA products.

FIG. 7. Next-generation SOLiD sequencing of cDNAs synthesized from miRNAx via group II intron RT template switching under reaction conditions that decrease non-templated nucleotide addition. Synthesis and cloning of cDNAs (SEQ ID NO: 28) corresponding to the miRNAx template (SEQ ID NO: 7) with randomized nucleotide residues at the 5' and 3' termini was done as in FIG. 3, except that miRNAx oligonucleotide was synthesized with hand-mixed nucleotides to obtain more even ratios of nucleotide residues at the randomized positions, and the reverse transcription reaction was done in 450 mM NaCl, 5 mM MgCl$_2$, 20 mM Tris-HCl, pH 7.5 with 1 mM dNTPs for 10 min at 60° C. The cDNAs were cloned via the CircLigase procedure, using CircLigase II, as described in FIG. 2, and analyzed by SOLiD sequencing. The SOLiD sequences (SEQ ID NOS 117-136, respectively, in order of appearance) shown are the 20 most frequent among 2,239,072 high-quality reads, with the numbers to the right indicating the number of reads for that sequence. All sequences correspond to molecules resulting from a single template switch from the IA-P1 RNA/Pc DNA template-primer substrate ("IA-P1 RNA" sequence disclosed as SEQ ID NO: 27) to miRNAx. Nucleotide positions that had been randomized are indicated in underlined and shaded letters; mutant nucleotide residues are shown in lower-case letters, and non-templated nucleotide residues are shown in bold lower-case letters. Similar results were obtained by Sanger sequencing (not shown).

having different single nucleotide 3' overhangs (A, C, G, T, or an equimolar mixture of all four nucleotides (N)) to target miRNAx's (SEQ ID NO: 137) having different 3' nucleotide residues (A, C, G, or U). Reactions were with 2 μM TeI4c-MRF RT for 10 min at 60° C. in a high-salt reaction medium (450 mM NaCl, 5 mM MgCl$_2$, 20 mM Tris-HCl, pH 7.5, 1 mM DTT, 1 mM dNTPs), which reduces non-templated nucleotide addition by the RT. The products were analyzed in a denaturing 20% polyacrylamide gel, which was scanned with a PhosphorImager™. Numbers to left of gel indicate positions of labeled size markers (10-bp ladder). *, $^{32}$P-label at 5' end of primer. (B) Template switching from IA-P1 RNA/Pc DNA with equimolar single-nucleotide 3' overhangs to an miRNAx with a 3' phosphorylated C residue before and after dephosphorylation with T4 polynucleotide kinase (P and DP, respectively) or to a DNA oligonucleotide of identical sequence (miDNAx).

Figure 10:
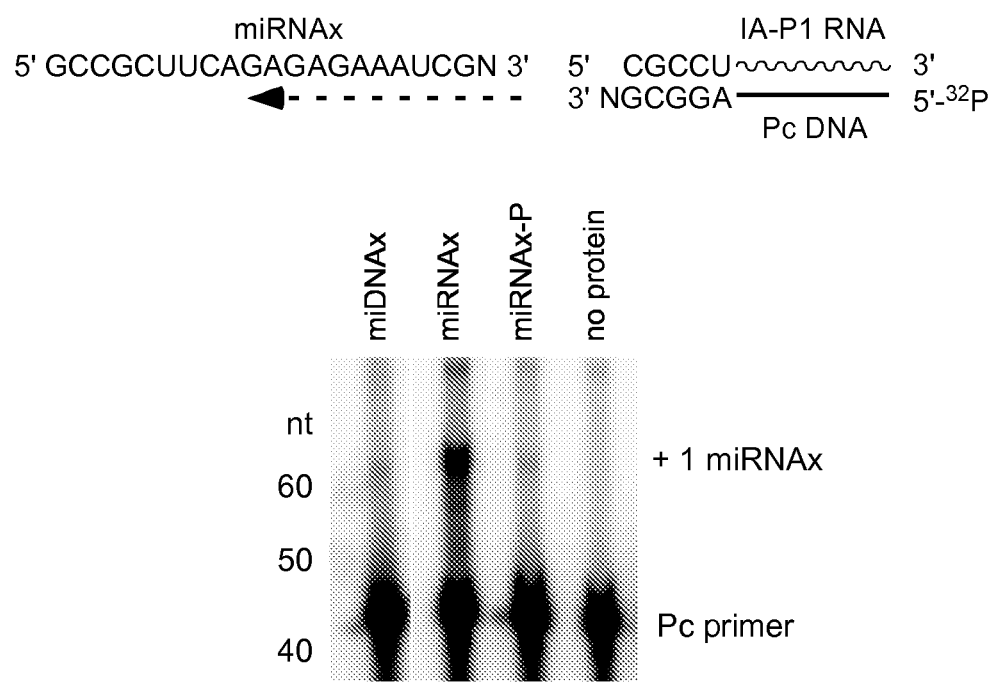

FIG. 10. Template-switching of group II intron RT GsI-IIC-MRF from 3'-overhang substrates. Template switching from IA-P1 RNA/Pc DNA with equimolar A, C, G, or T single nucleotide 3' overhangs to an miRNAx (SEQ ID NO: 137) with (P) or without a 3' phosphorylated C residue or to a DNA oligonucleotide of identical sequence (miDNAx). Reactions were with 2 μM GsI-IIc-MRF for 10 min at 60° C. in a high-salt reaction medium (450 mM NaCl, 5 mM MgCl$_2$, 20 mM Tris-HCl, pH 7.5, 1 mM DTT, 1 mM dNTPs). The products were analyzed in a denaturing 20% polyacrylamide gel, which was scanned with a PhosphorImager™. Numbers to left of gel indicate positions of labeled size markers (10-bp ladder.)*, $^{32}$P-label at 5' end of primer.

Figure 11:
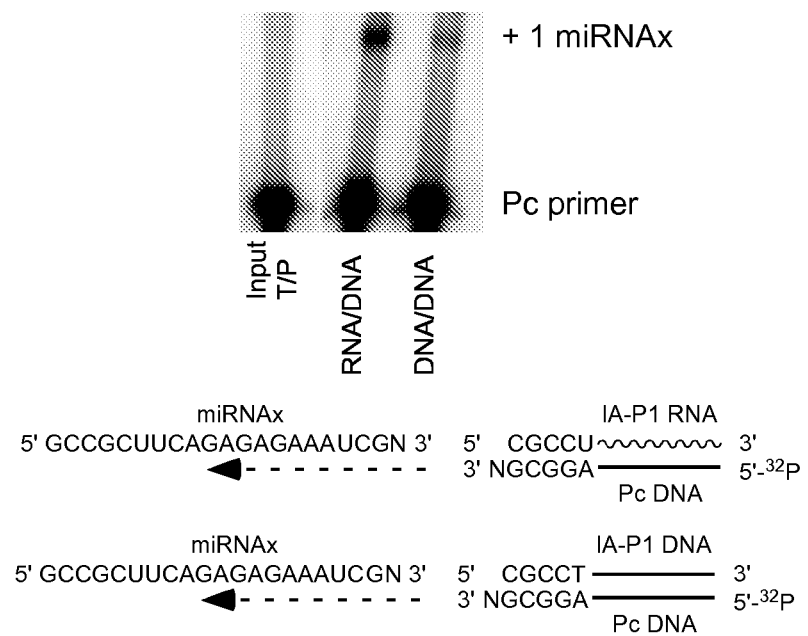

FIG. 11. Template-switching of TeI4c-MRF RTs from RNA/DNA or DNA/DNA template primers. Template-switching reactions were done with $^{32}$P-labeled DNA primer substrates (IA-P1 RNA/Pc 3'-overhang DNA) having an equimolar mixture of A, C, G, or T single nucleotide 3' overhangs annealed to either IA-P1 RNA or DNA. Reactions were with 2 μM TeI4c-MRF RT for 10 min at 60° C. in a high-salt reaction medium (450 mM NaCl, 5 mM MgCl$_2$, 20 mM Tris-HCl, pH 7.5, 1 mM DTT, 1 mM dNTPs). The products were analyzed in a denaturing 20% polyacrylamide gel, which was scanned with a PhosphorImager™. *, $^{32}$P-label at 5' end of primer. The arrow indicates the template switching product. FIG. 11 discloses the "miRNAx" sequence as SEQ ID NO: 137.

Figure 9:
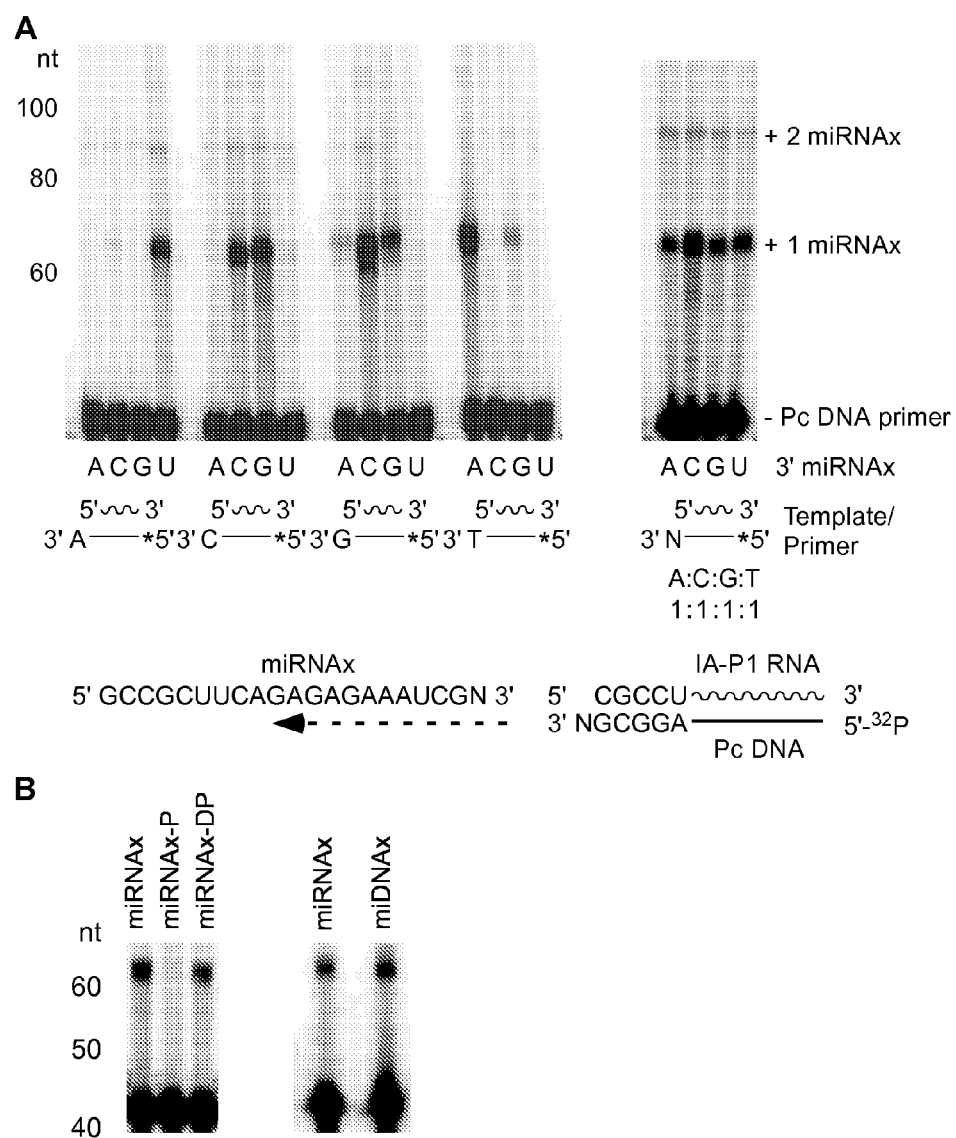
FIG. 9 Template-switching of group II intron TeI4c-MRF RT from 3'-overhang substrates. (A) Template-switching reactions were done with initial $^{32}$P-labeled RNA template/DNA primer substrates (IA-P1 RNA/Pc 3'-overhang DNA)
Figure 12:
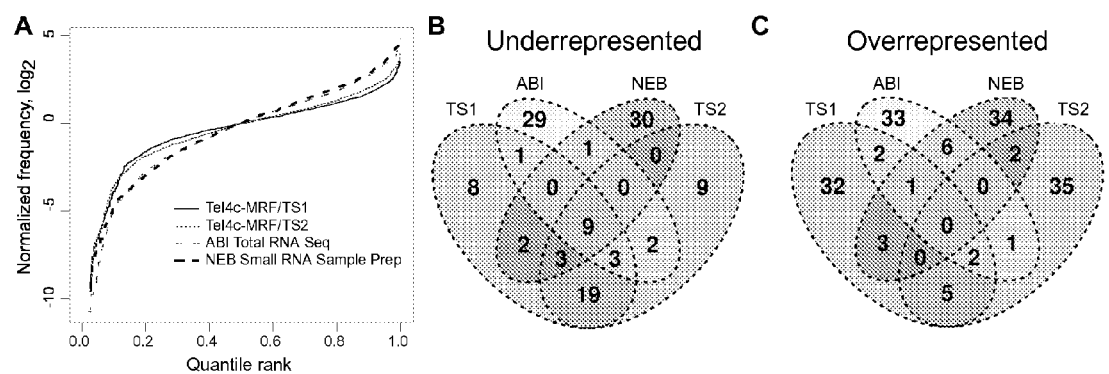

FIG. 12. Cloning and sequencing of miRNAs by using group II intron RT template switching. Template-switching reactions were done with TeI4c-MRF RT (2 kM) to a miRNA reference set (963 eqimolar miRNAs, 110 nM; Miltenyi miRXplore) from an initial IA-P1 RNA template/Pc DNA primer substrate (100 nM). The latter had single A, C, G, or T 3'-overhangs mixed at an equimolar ratio (TS1) or at 2:0.5:1:1 (TS2) to adjust the representation of miRNAs with 3' U- or G-residues (see FIG. 9). Reactions were done as in FIG. 9, and cDNAs were cloned as described in FIG. 2. Parallel RNA-seq libraries were prepared from equal aliquots of the miRNAs by using either a Total RNA-Seq kit (Applied Biosystems™; ABI) or small RNA sample prep set 3 kit (New England BioLabs®; NEB). These kits ligate adaptors for SOLiD sequencing to the miRNA 3' and 5' ends simultaneously (ABI) or sequentially (NEB) and reverse transcribe with ArrayScript or SuperScript II using a DNA primer complementary to the 3' adaptor. (A) Plots showing counts for a subset of 898 miRNA with uniquely identifiable core sequences ranked from the least to most abundant, median normalized, log$_2$ transformed, and plotted to compare variance introduced by the library preparation method. (B) and (C) Venn diagrams showing overlap between under- and over-represented miRNAs in the different RNA-seq libraries. The 5% least and most abundant miRNAs in each library were identified using R and plotted using the VennDiagram R package (Chen & Boutros 2011).

Figure 13:
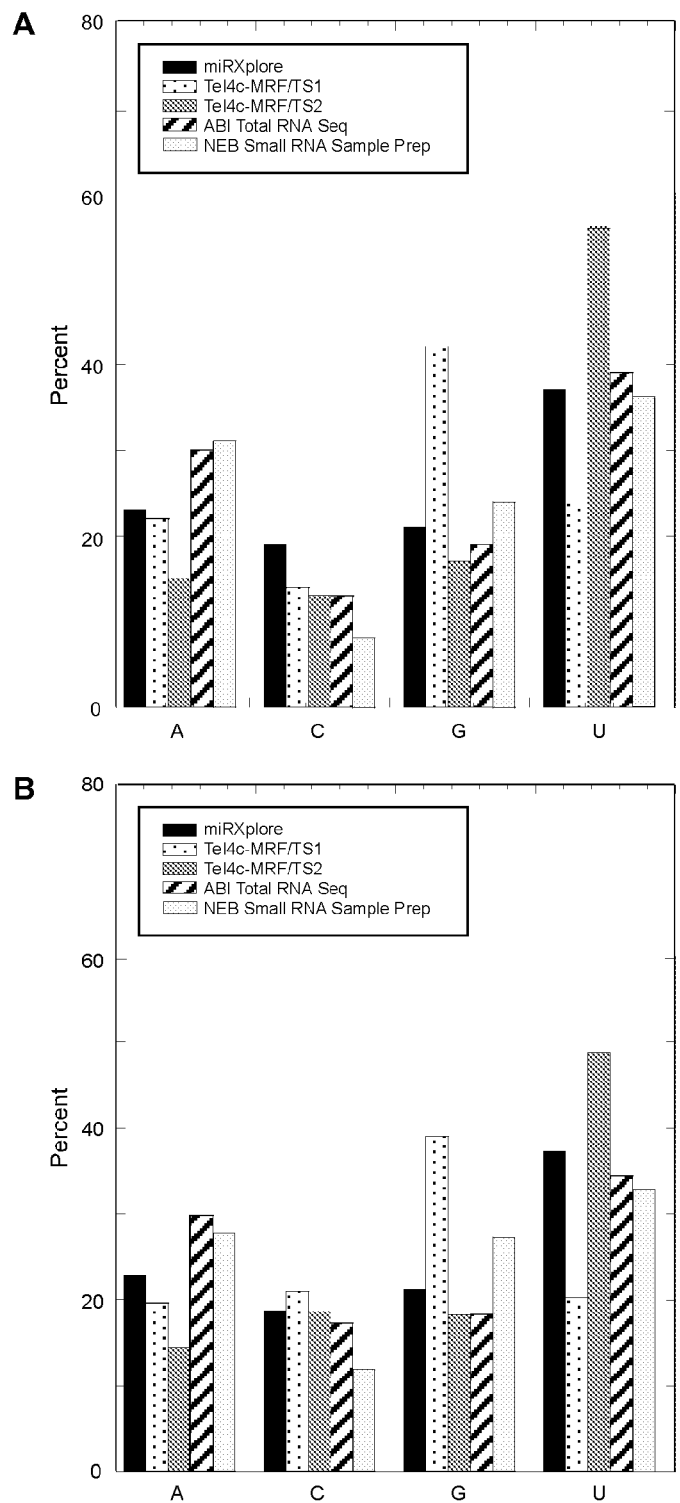

FIG. 13. Representation of miRNA 3'-terminal nucleotide residues in RNA-seq libraries prepared by group II intron RT template switching and two commercial kits. RNA-seq libraries were prepared by template switching with TeI4c-MRF RT; a Total RNA-Seq kit (Applied Biosystems™); or a small RNA sample prep set 3 kit (New England BioLabs®). The template-switching reactions with TeI4c-MRF RT were done by using IA-P1 RNA/Pc DNA template/primer substrates with single A, C, G, or T 3'-overhangs mixed either at a equimolar ratio (TS1) or at a ratio of 2:0.5:1:1 (TS2) to adjust the representation for miRNAs with 3' U- or G-residues. The bar graphs compare the percentage of miRNAs ending in each of the four bases in the miRXplore reference set (black) with the percentage of that base at the 3' end of miRNAs in the RNA-seq libraries (TeI4c-MRF/TS1, dotted; TeI4c-MRF/TS2, dark grey; ABI Total RNA Seq, angled lines; NEB Small RNA Sample Prep, light grey). In panel A, the 3'-nucleotide residue of miRNAs in the RNA-seq libraries was identified as the base prior to the Internal Adaptor. To avoid primer-dimer, adaptor-only, and low quality sequences, a perfect match to 8 bases of the Internal Adaptor no closer than 15 bp from the start of each sequence was required when determining the terminal base in each sample. In panel B, the 3'-nucleotide residue of the miRNAs in the RNA-seq libraries was inferred from the abundance-adjusted distribution of 3'-nucleotide residues for the set of 898 miRNAs with unique core sequences (see FIG. 12). Similar trends are seen for both methods of identifying the 3'-terminal residue of the miRNA.

DETAILED DESCRIPTION OF THE INVENTION

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

DEFINITIONS

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

An "isolated" polynucleotide, as used herein, means a polynucleotide that has been either removed from its natural environment, produced using recombinant techniques, or chemically or enzymatically synthesized. A polynucleotide can also be purified, i.e., essentially free from any other polynucleotides and associated cellular products or other impurities.

A nucleotide (nt) consists of a phosphate group linked by a phosphoester bond to a pentose (ribose in RNA, and deoxyribose in DNA) that is linked in turn to an organic base. The monomeric units of a nucleic acid are nucleotides. Naturally occurring DNA and RNA each contain four different nucleotides: nucleotides having adenine, guanine, cytosine and thymine bases are found in naturally occurring DNA, and nucleotides having adenine, guanine, cytosine and uracil bases are found in naturally occurring RNA. The bases adenine, guanine, cytosine, thymine, and uracil often are abbreviated A, G, C, T and U, respectively.

Complementary nucleotides are those which readily form base pairs in double stranded oligonucleotides. Adenine is complementary with thymine or uracil, and vice-versa, and guanine is complementary with cytosine, and vice-versa. Complementarity refers to the likelihood that opposing nucleotides in adjacent strands are complementary, with high complementarity indicating a high number of complementary nucleotides, and low-complementarity referring to a lower number of complementary nucleotides.

Nucleotides include free mono-, di- and triphosphate forms (i.e., where the phosphate group has one, two or three phosphate moieties, respectively). Thus, nucleotides include ribonucleoside triphosphates (e.g., ATP, UTP, CTG and GTP) and deoxyribonucleoside triphosphates (e.g., dATP, dCTP, dITP, dGTP and dTTP), and derivatives thereof. Nucleotides also include dideoxyribonucleoside triphosphates (ddNTPs, including ddATP, ddCTP, ddGTP, ddITP and ddTTP), and derivatives thereof.

A polynucleotide, as used herein, may mean any molecule including a plurality of nucleotides, including but not limited to DNA or RNA. Preferably, the polynucleotide includes at least 5 nucleotides, and more preferably it includes 10 or more nucleotides. The depiction of a single strand also defines the sequence of the complementary strand. Thus, a nucleic acid also encompasses the complementary strand of a depicted single strand. A polynucleotide may be single stranded or double stranded, or may contain portions of both double stranded and single stranded sequence. Double stranded polynucleotides are a sequence and its complementary sequence that are associated with one another, as understood by those skilled in the art. The polynucleotide may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine, hypoxanthine, isocytosine and isoguanine. Polynucleotides may be obtained by chemical synthesis methods or by recombinant methods. When a polynucleotide has been defined as consisting of either DNA or RNA, it may be referred to as a DNA strand, or RNA strand, respectively.

An oligonucleotide, when used herein, refers to a polynucleotide as defined herein, except that oligonucleotides are generally smaller in length. An oligonucleotide includes a plurality of nucleotides, and therefore has a minimum size of 2 nucleotides, with a minimum of 6 nucleotides in some embodiments. With regard to their maximum size, oligonucleotides generally have a size of 100 nucleotides or less, with the limit being 70 nucleotides or less in some embodiments.

An "overhang sequence," as that term is used herein, refers to a single stranded region of nucleic acid extending from a double stranded region.

The term "primer", as used herein, refers to an oligonucleotide, occurring naturally as in a purified restriction digest or produced synthetically that is characterized by an ability to be extended against a template oligonucleotide, so that an oligonucleotide whose sequence is complementary to that of at least a portion of the template molecule is linked to the primer, when all are placed in the presence of nucleotides at a suitable temperature and pH. However, the mere ability to be used in this fashion does not require that primers be fully extended against a template, and in some embodiments, primers are used only as a site for the addition of a small number of non-templated nucleotides. Primers such as primer hexamers having a length of at least 6 nucleotides long can be used. Preferred primers have a length within the range of about 6-100 nucleotides, or in some embodiments from 10 to 70 nucleotides. However, larger primers can be used in some embodiments. These larger primers are polynucleotides, as defined herein.

"Identical" or "identity" used herein in the context of two or more oligonucleotides, may mean that the sequences have a specified percentage of residues that are the same over a region of comparison. The percentage may be calculated by optimally aligning the two sequences, comparing the two sequences over the specified region, determining the number of positions at which the identical residue occurs in both sequences to yield the number of matched positions, dividing the number of matched positions by the total number of positions in the region of comparison, and multiplying the result by 100 to yield the percentage of sequence identity. "Substantially similar" means that a given nucleic acid sequence shares at least 85%, more preferably at least 90%, and even more preferably at least 95% identity with a reference sequence. In cases where the two sequences are of different lengths or the alignment produces one or more staggered ends and the specified region of comparison includes only a single sequence, the residues of single sequence may be included in the denominator but not the numerator of the calculation. When comparing DNA and RNA, thymine (T) and uracil (U) may be considered equivalent. Identity determination may be performed manually or by using a computer sequence algorithm such as BLAST or BLAST 2.0.

As used herein, the term "polymerase chain reaction" ("PCR") refers to a method for increasing the concentration of a segment of a target sequence in a mixture of DNA sequences without cloning or purification. See for example Bartlett & Stirling (2003), which provides an overview of PCR and its development. This process for amplifying the target sequence typically consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To amplify the target sequence, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times to obtain a high concentration of an amplified segment of the desired target sequence. Unless otherwise noted, PCR, as used herein, also includes variants of PCR such as allele-specific PCR, asymmetric PCR, hot-start PCR, ligation-mediated PCR, multiplex-PCR, reverse transcription PCR, or any of the other PCR variants known to those skilled in the art.

As used herein, the term "template switching" refers to the ability of a reverse transcriptase to switch from an initial nucleic acid sequence template to the 3' end of a new nucleic acid sequence template having little or no complementarity to the 3' end of the cDNA synthesized from the initial template. A salient example of template switching herein is the ability of a reverse transcriptase to switch from an initial nucleic acid sequence template/primer substrate to the 3' end of a new nucleic acid sequence template having little or no complementary to the 3' end of the DNA primer strand.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

In one aspect, a method of preparing a DNA copy of a target polynucleotide using template switching is provided. Template switching allows a DNA copy to be prepared using a reverse transcriptase that switches from an initial nucleic acid sequence template to the 3' end of a new nucleic acid sequence template having little or no complementarity to the 3' end of the DNA synthesized from the initial template, thereby allowing the synthesis of a continuous product DNA that directly links an adaptor sequence to a target oligonucleotide sequence without ligation.

The target polynucleotide can be various different nucleic acid sequences. The target polynucleotide can be made of RNA (e.g., a miRNA) or the target polynucleotide can be made of DNA. The size and sequence of the polynucleotide are not particularly limited for the methods described herein, though it is preferred that the target polynucleotide have a size of at least 10 nucleotides.

The method of preparing a DNA copy of a target polynucleotide includes mixing a double stranded template/primer substrate with a target polynucleotide in a reaction medium. The double stranded template/primer substrate consists of a DNA primer oligonucleotide associated with a complementary oligonucleotide template strand. While the double stranded template/primer substrate typically includes strands that are oligonucleotides, in additional embodiments one or both of the strands can be polynucleotides, as defined herein. The DNA primer and template strands can include adaptor sequences, and may also include other sequences that provide a useful functionality for the target polynucleotide. For example, the primer can include a sequence that facilitates detection, identification, PCR amplification, and/or cloning of the target polynucleotide. Primer strands can also contain affinity tags for easy purification or tags that can link the primer to a solid surface. Primer and complementary template oligonucleotides can contain modifications that prevent them from being copied. The primer can also be a polynucleotide having a hairpin configuration. Examples of useful primer strands include Illumina® small RNA primers, Multiplex sequencing primers, Roche® 454 primers, NexTera™ primers and custom designed primers to enrich for sequences of interest, such as optimus primers.

The joining of the DNA primer oligonucleotide to the target polynucleotide is initiated by adding a suitable amount of a non-retroviral reverse transcriptase to the reaction medium. Suitable amounts are known to those skilled in the art, and are provided in examples herein. This causes the reverse transcriptase to extend the DNA primer oligonucleotide from its 3' end to make a DNA copy strand that creates a complementary target DNA polynucleotide that is synthesized using the target polynucleotide as a template.

The term "reverse transcriptases" (i.e., RNA-directed DNA polymerases) refers to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transciptases, and group II intron reverse transcriptases. Examples of group II intron reverse transcriptases include the *Lactococcus lactis* L1.LtrB intron reverse transcriptase, the *Thermosynechococcus elongatus* TeI4c intron reverse transcriptase, or the *Geobacillus stearothermophilus* GsI-IIC intron reverse transcriptase. Further bacterial reverse transcriptases are described by Simon & Zimmerly (2008), and Kojima and Kanehisa (2008), which describe many classes of non-retroviral reverse transcriptases (i.e., retrons, group II introns, and diversity-generating retroelements among others). Reverse transcriptase has been used primarily to transcribe RNA into cDNA, which can then be cloned into a vector for further manipulation or used in various amplification methods such as polymerase chain reaction, nucleic acid sequence-based amplification (NASBA), transcription mediated amplification (TMA), self-sustained sequence replication (3SR), diverse primer extension reactions, 5'RACE, detection of chemical modifications or other techniques that require synthesis of DNA using an RNA template.

In addition to their usually expressed form, functional fragments of reverse transcriptases can also be used. The functional domains of reverse transcriptases are well-known to those skilled in the art, and functional fragments can be prepared that do not include the structure of the reverse transcriptase. For example, subclones of the gene encoding a known reverse transcriptase can be produced using conventional molecular genetic manipulation for subcloning gene fragments, such as described by Sambrook et al. (1989), and Ausubel et al. (1999 and preceding editions). The subclones are then expressed in vitro or in vivo in bacterial cells to yield a smaller protein or polypeptide that can be tested for reverse transcriptase activity to determine if it is a functional fragment of reverse transcriptase.

In some embodiments, the non-retroviral reverse transcriptase is a group II intron reverse transcriptase. A wide variety of group II intron-derived reverse transcriptases are known. See for example the Zimmerly Lab Website for Mobile Group II Introns that describes 105 full length group II intron-derived reverse transcriptases. The use of this website is described by Dai et al. (2003) and Candales et al. (2012). In further embodiments, mobile group II intron reverse transcriptases or stabilized reverse transcriptase fusion proteins can be used. Stabilized reverse transcriptase fusion proteins are reverse transcriptases that have been stabilized by attachment to a protein such as a maltose binding protein. Exemplary methods for the preparation of stabilized reverse transcriptase fusion proteins is described further herein in Examples 1 and 2. A more complete description of stabilized reverse transcriptase fusion proteins is found in US Patent Publication No. 2012/0009630.

Group II introns encode a class of RNAs known for their self-splicing reaction. Under certain in vitro conditions, group II intron-encoded RNAs can excise themselves from precursor RNAs and ligate together their flanking exons, without the aid of a protein. The splicing reaction mechanism is similar to the splicing of nuclear pre-mRNA introns. A number of group II introns also encode reverse transcriptase (RT) open reading frames (ORF) and are active mobile elements. The ORF is typically found in domain DIV of the group II intron encoded RNA. The group II intron RT assists RNA splicing by stabilizing the catalytically active RNA structure and then remains bound to the excised intron RNA in a ribonucleoprotein (RNP) that promotes intron mobility by a process termed "retrohoming." Retrohoming occurs by a mechanism in which the excised intron RNA in the RNPs inserts directly into a DNA target site and is reverse transcribed by the RT. During retrohoming, in which the group II intron facilitates targeting of the intron to appropriate DNA sequences, the group II intron RT must produce an accurate cDNA copy of the intron RNA, which is typically 2-2.5 kb long and folds into highly stable and compact secondary and tertiary structures. Thus, group II intron RTs must have high processivity and fidelity in order to carry out their biological function. Group II intron-derived RTs also lack RNase H activity, which can be beneficial because RNase H specifically degrades the RNA of RNA:DNA hybrids, which allows any RNA to be copied only once and can lead to reduced yields of full length cDNA.

Template switching from the DNA primer oligonucleotide to the target polynucleotide by a non-retroviral reverse transcriptase is carried out in a reaction medium. The reaction medium includes, or can be made to include during the method, a sufficient amount of deoxy- or dideoxyribonucleoside triphosphates to allow the DNA copy to be made, and should be kept at a temperature suitable for operation of the non-retroviral reverse transcriptase (e.g., 25° C. to about 81° C.). Buffers and other materials necessary for operation of the reverse transcriptase in an aqueous medium are also included in amounts known to those skilled in the art, for example a buffer containing 20 mM Tris pH 7.5, 10 mM $MgCl_2$, 75 mM KCl, and 1 mM DTT (Levesque-Sergerie et al. 2007).

The double stranded template/primer substrate that is used to facilitate formation of the DNA copy is made up of a DNA primer oligonucleotide associated with a complementary oligonucleotide template strand. In some embodiments, the complementary oligonucleotide template strand can be made of RNA to provide a complementary RNA strand. In other embodiments, the complementary oligonucleotide can be made of DNA to provide a complementary DNA strand. Preferably, the complementary oligonucleotide template strand is made of RNA because it is used more efficiently, most likely because the natural template of the reverse transcriptase is RNA. However, DNA can also be used. See for example FIG. 11, which shows template switching using either RNA/DNA or DNA/DNA template primers.

The end of the double stranded template/primer substrate which is extended by reverse transcriptase can be blunt, which means that the 3' end of the DNA primer oligonucleotide and the 5' end of the complementary oligonucleotide template strand can end at the same position, or be "directly aligned," with no unpaired nucleotides. Alternately, the same end of the double stranded template/primer substrate can have an "overhang" in which the 3' end of the DNA primer oligonucleotide extends 1 nucleotide beyond the 5' end of the complementary oligonucleotide template strand. The requirement for only a single overhang, or a blunt end, for template switching provides an advantage over retroviral reverse transcriptases, which require at least two base pairs between the 3' end of the DNA primer strand and the 3' end of the new RNA template in order to template switch (Oz-Gleenberg et al. 2011). A single nucleotide overhang can be used to specifically template switch to a nucleic acid with a complementary 3' end, or an empirically designed mixture of all four overhangs can be used to reduce bias in template switching. An advantage of single nucleotide overhangs over blunt ends is that the ratio of nucleotides making up the overhangs can be adjusted as desired to be complementary to the 3' nucleotide residue of a single target polynucleotide or to the 3' nucleotide residues of a mixture of target polynucleotides. When an overhang is present, it is preferable that the nucleotide at the 3' end of the target polynucleotide be complementary to the overhang nucleotide at the 3' end of the DNA primer strand, to facilitate association through base pairing of these two nucleotides.

An "overhang" can also be provided at a different position while carrying out some embodiments of the methods described herein. In these embodiments, the non-retroviral reverse transcriptase adds 1-15 additional non-complementary nucleotides at the 3' end of the DNA primer oligonucleotide before creating the DNA copy polynucleotide that includes a complementary target DNA polynucleotide. Because these nucleotides are not associated with another strand, they are non-complementary when added, although of course it would be possible for them to become complementary should a target polynucleotide having the appropriate sequence become available. In additional embodiments, the overhang at the 3' end of the DNA primer oligonucleotide can be shorter than 1-15 nucleotides. For example, it can be 1-6 nucleotides, 1-3 nucleotides, or it can be a single nucleotide.

In some embodiments, it may be desirable to provide an overhang at the 3' end of the DNA primer oligonucleotide outside of the context of copying a target polynucleotide. Accordingly, the present disclosure also provides a method of adding additional nucleotides to a DNA primer oligonucleotide. This method involves adding a suitable amount of a non-retroviral reverse transcriptase to a reaction medium that includes a double stranded template/primer substrate, consisting of a DNA primer oligonucleotide associated with a complementary oligonucleotide template strand, as described herein, and then allowing the non-retroviral reverse transcriptase to add 1-15 additional non-complementary nucleotides at the 3' end of the DNA primer oligonucleotide. In some embodiments of this method, the non-retroviral reverse transcriptase is a group II intron reverse transcriptase. In further embodiments, it may be preferable to add only 1-6 additional non-complementary nucleotides, or even a single non-complementary nucleotide to the 3' end of the DNA primer oligonucleotide.

Certain embodiments of the methods described herein can include a blocking agent at the 3' end of the complimentary oligonucleotide template strand to terminate the oligonucleotide and impede further recopying by the reverse transcriptase. The blocking agent impedes the reverse transcriptase from using this oligonucleotide as a target. Examples of suitable blocking agents include 3'-amino-modifier C3 and 3'-amino-modifier C7, both of which contain branched linkers in which the amino group is protected with the fluorenylmethoxycarbonyl (Fmoc) group. Other potential 3' modifiers could be thiol groups; DPTA (3,3'-(hydroxynitrosohydrazino)bis-1-propanamine), which can be also used to conjugate the oligonucleotide to gold surfaces; spacer phosphoamidite modifiers; or glycerol. Spacer modifiers could be made photocleavable. Use of blocking agents to prevent recopying is understood by those skilled in the art, and therefore other blocking agents may be employed with the methods described herein.

One of the advantages of joining a primer to a target polynucleotide using template switching is the ability to associate a suitable primer with a wide variety of differing polynucleotides simultaneously. Accordingly, the method described herein can be used to prepare a cloning library having a plurality of DNA copy polynucleotides. The cloning library is prepared by mixing a double stranded template/primer substrate, as described herein with a plurality of different target polynucleotides in a reaction medium and adding a suitable amount of a non-retroviral reverse transcriptase to the reaction medium to form a library of DNA polynucleotides complementary to the target polynucleotides that include a sequence (e.g., an adaptor sequence) to facilitate subsequent copying and/or identification. Any number of additional target polynucleotides can be included. For example, 2, 5, 10, 50, 100, or more different target oligonucleotides can be simultaneously associated with adaptor sequences using the methods described herein.

Additional embodiments can also include the further step of circularizing the DNA copy polynucleotide. Circularizing the strand refers to connecting the 3' with the 5' end of the DNA copy polynucleotide to result in a DNA ring rather than a linear polynucleotide strand. Circularization can be carried out, for example, by treating the DNA copy polynucleotide with a CircLigase (e.g., CircLigase I or CircLigase II), an enzyme that circularizes single-stranded DNA. Circularization of the DNA allows the strand to be readily amplified by using PCR and bidirectional primers.

The reverse transcriptase (e.g., a group II intron reverse transcriptase) and double stranded template/primer substrate can be incorporated into a kit that is useful for the preparation of a DNA copy polynucleotide or for non-templated nucleotide addition. The double stranded template/primer substrate can include a blunt or overhanging end, as previously described. Such a kit may include a carrier device compartmentalized to receive one or more containers, such as vials, tubes, and the like, each of which includes one of the separate elements used to prepare the DNA copy polynucleotide. For example, there may be provided a first container, the contents of which include the reverse transcriptase in solution. Further, any number of additional containers can be provided, the contents of which independently may include a double stranded template/primer substrate and components of the reaction medium, such as suitable buffers and nucleotides for DNA synthesis such as the deoxynucleotide triphosphates (e.g., dATP, dCTP, dGTP, and dTTP). The kit can also include one or more target polynucleotides, or the kit may be configured to be used in conjunction with target polynucleotides that are provided from another source. Any combinations of the above components can be provided. The kit may be constructed to provide for stable storage of its various components, while allowing a reverse transcriptase to be added to the reaction medium to extend the DNA primer oligonucleotide of the double stranded template/primer substrate from its 3' end to provide a DNA copy polynucleotide that includes a complementary target DNA polynucleotide that is synthesized using the target polynucleotide as a template.

The following examples provide methods of preparing non-retroviral reverse transcriptases and using them to link a DNA primer oligonucleotide to a target polynucleotide using template switching or add additional nucleotides to the template/primer substrate. These examples are included for purposes of illustration and are not intended to limit the scope of the invention.

EXAMPLES

Example 1

Preparation of TeI4c-MRF and GsL-IIc RTs

The expression plasmid pMalE-RF-TeI4c contains the RT ORF of the *Thermosynechococcus elongatus* TeI4c group II intron with a fused N-terminal MalE tag cloned behind the tac promoter in pMal-c2t, a derivative of pMal-c2x (New England Biolabs®, Ipswich, Mass.) with a TEV protease-cleavage site in place of the factor Xa site (Kristelly et al. 2003). The plasmid was constructed by PCR amplifying the TeI4c RT ORF of the TeI4c intron cloned in pUC19 (Mohr et al. 2010) with primers that append restriction sites (EcoRI and PstI), and then cloning the PCR products into the corresponding sites of pMal-c2t. The TEV-protease cleavable linker (TVDEALKDAQTNS$_3$N$_{10}$LENLYFQG) (SEQ ID NO: 3) was replaced with a rigid linker (TVDAALAAAQT-NAAAAA) (SEQ ID NO: 4) by the Quick Change PCR procedure, using Accuprime polymerase (Invitrogen™; Makarova et al. 2000).

pMalE-GsI-IIC was constructed by PCR amplifying the RT ORFs from *Geobacillus stearothermophilus* strain 10 genomic DNA (obtained from Greg Davis, Sigma-Aldrich) with primers that appended BamHI sites and cloning the PCR product between the corresponding sites of pMal-c2t. GsI-IIC is a group IIC intron found in multiple copies in the *G. stearothermophilus* genome (CP001794, Moretz and Lampson 2010). The cloned GsI-IIC RT ORF corresponds to one of these genomic sequences and has three amino acid sequence changes compared to the RT ORF cloned by Vellore et al. (2004).

The MalE-RF RTs were expressed from pMalE-RF-TeI4c or pMalE-RF-GsI-IIc in *Escherichia coli* Rosetta 2 (Novagen®, EMD Biosciences, Gibbstown N.J.) or ScarabX-press® T7lac (Scarab Genomics™, Madison Wis.). The *E. coli* strains were transformed with the expression plasmid, grown at 37° C. in TB or LB medium to mid-log phase (O.D.$_{600}$=0.8), and induced by adding 1 mM isopropyl 3-D-1-thiogalactopyranoside (IPTG) and incubating at 18° C. for ~24 h. The cells were then pelleted by centrifugation, resuspended in 45 ml of buffer A (20 mM Tris-HCl, pH 7.5, 0.5 M KCl, 1 mM EDTA, 1 mM dithiothreitol, and 10% glycerol), and frozen at −80° C.

For purification of the MalE-RF RTs, the cell suspension was thawed, treated with lysozyme (1 mg/ml; Sigma-Aldrich, St. Louis Mo.) for 15 min on ice, freeze-thawed three times on dry ice, sonicated (Branson 450 Sonifier, Branson Ultrasonics, Danbury Conn.; three or four 10 sec bursts on ice at an amplitude of 60%, with 10 sec between bursts), and centrifuged for 30 min at 18,500×g at 4° C. Nucleic acids were precipitated by adding polyethyleneimine (PEI) to a final concentration of 0.2% and centrifuging for 15 min at 15,000×g at 4° C. The resulting supernatant was applied to an amylose column (10-ml column volume; Amylose High-Flow; New England Biolabs™, Ipswich, Mass.), which had been equilibrated in buffer A, and the column was washed with five column volumes each of buffer A containing 0.5 M, 1.5 M, and 0.5 M KCl, and then eluted with buffer A containing 10 mM maltose, Pooled protein fractions were purified further by heparin-Sepharose chromatography (3 tandem 1-ml columns; GE Healthcare Biosciences™ Corp.), which had been pre-equilibrated in 20 mM Tris-HCl, pH 7.5 containing 100 mM KCl, 1 mM EDTA, 1 mM DTT, 10% glycerol. The proteins were applied to the column in the buffer A and eluted with a 40-column volume gradient from the loading concentration to 2 M KCl. The peak fractions were pooled and dialyzed against 20 mM Tris-HCl, pH 7.5, 0.5 M KCl, 1 mM EDTA, 1 mM DTT, and 50% glycerol, flash frozen, and stored at −80° C.

Example 2

Preparation of the L1.LtrB Group II Intron RT (LtrA Protein)

The LtrA protein was expressed in *E. coli* BL21(DE3) from the plasmid pMAL-LtrA, which contains the LtrA ORF (Mills et al. 1996) cloned downstream of a tac promoter and Φ10 Shine-Dalgarno sequence between BamHI and HindIII of the protein-expression vector pMAL-c2t (see above). A starter culture of cells was grown in LB medium overnight at 37° C. and used to inoculate ultra yield flasks containing 0.5 L of LB medium, which were autoinduced by growing at 37° C. for 3 h followed by 18° C. for 24 h (Studier 2005). Cells were harvested by centrifugation (Beckman JLA-8.1000; 4,000×g, 15 min, 4° C.) and resuspended in 1 M NaCl, 20 mM Tris-HCl pH 7.5, 20% glycerol, and 0.1 mg/ml lysozyme (Sigma-Aldrich®, St. Louis, Mo.). Lysis was achieved through 3 freeze-thaw cycles and sonication as described above for preparation of the Tel4c-MRF RT. After pelleting cell debris (Beckman Coulter™ JA-14 rotor, 10,000 rpm, 30 min, 4° C.), nucleic acids were precipitated from the supernatant with 0.4% polyethylenimine (PEI) and constant stirring for 20 min at 4° C., followed by centrifugation (Beckman Coulter™ JA-14 rotor, 14,000 rpm, 30 min, 4° C.). Proteins were then precipitated from the supernatant by adding ammonium sulfate to 50% saturation with constant stirring for 1 h at 4° C. The precipitated protein was pelleted (Beckman Coulter™ JA-14 rotor, 14,000 rpm 30 min, 4° C.) and dissolved in 500 mM NaCl, 20 mM Tris-HCl pH 7.5, 10% glycerol. The protein was applied to a 10-ml amylose column (Amylose High-Flow resin; New England Biolabs™, Ipswich, Mass.), which was washed with 3 column volumes of 500 mM NaCl, 20 mM Tris-HCl pH 7.5, 10% glycerol and eluted with 500 mM NaCl, 20 mM Tris-HCl pH 7.5, 10% glycerol containing 10 mM maltose. Fractions containing MalE-LtrA were incubated with 80 g/ml TEV protease for 18 h at 4° C. These fractions were further purified from the TEV protease by FPLC through a Ni-NTA column loaded with 40 mM imidazole, washed with 3 column volumes of 500 mM NaCl, 20 mM Tris-HCl pH 7.5, 10% glycerol, 40 mM imidazole and eluted in 500 mM NaCl, 20 mM Tris-HCl pH 7.5, 10% glycerol, 300 mM imidazole. Monomeric LtrA was further purified by FPLC through a column with heparin Sepharose (New England Biolabs®). The purified protein was then concentrated to 30 µM and exchanged into 100 mM NaCl, 20 mM Tris-HCl pH 7.5, 10% glycerol by dialysis.

Example 3 cDNA Cloning and Sequencing Via Group II Intron RT Template-Switching

Reverse transcription reactions with the Tel4c-MRF RT were performed by incubating the purified protein with artificial oligonucleotide substrates synthesized by Integrated DNA Technologies® (IDT; Coralville, Iowa). In some experiments, DNA primers were 5'-end labeled with [γ-$^{32}$P]-ATP (10 Ci/mmol; Perkin-Elmer®) using phage T4 polynucleotide kinase (New England Biolabs®) according to the manufacturer's protocol. Primers were annealed to RNA template strands by mixing at a 1.1:1 molar ratio in 10 mM Tris-HCl, pH 7.5, 1 mM EDTA, heating to 82° C. for 2 min, and then cooling to room temperature over 10 min using a PCR machine (Gene Amp 9700, Life Technologies™ Corporation, Carlsbad, Calif.). Reverse transcription reactions were done in 10-40 µl of reaction medium under conditions specified in the Figure Legends. The reactions were initiated by adding the enzyme and terminated by adding 125 mM EDTA, 0.05% SDS followed by phenol-CIA extraction. For experiments with labeled primers, the products were analyzed in a denaturing 20% polyacrylamide gel, which was scanned with a PhosphorImager™.

For cDNA cloning and sequencing via group II intron RT template switching, the inventors used a synthetic RNA template/DNA primer consisting of an IA-P1 RNA olgionucleotide with a 3' aminomodifier (AmMO, a primary amine attached via a linker of 6-7 carbons; IDT) (5'-CGCCUUG-GCCGUACAGCAGCCUCUC-UAUGGGCAGUCGGUGAU-AmMO-3') (SEQ ID NO. 5) annealed in a 1:1.1 molar ratio to 5'-labeled Pc primer containing a deoxyuridine (5'-ATCACCGACTGCCCATA-GAGAGCC/dU/GCTGTA 3') (SEQ ID NO. 6) was used. For reverse transcription reactions, the template/primer substrate (50 or 100 nM) was incubated with equimolar miRNAx (5' Phos-NNCGCUUCAGAGAGAAAUCNN 3') (SEQ ID NO. 7) and RT (2-2.5 µM final) in 50-100 µl of reaction medium under conditions described in Figure Legends. The resulting cDNAs were treated with a thermostable RNase H (Hybridase™; 20 units; Epicentre®) for 5 min at 55° C. cDNA products were band-isolated from a denaturing 20% polyacrylamide gel by crushing the gel slices and soaking them overnight in 0.5 M NH$_4$Cl, 0.1 M EDTA, 10 mM MOPS, pH 6.5, 0.1% SDS. The eluted cDNAs were phenol extracted, precipitated with 0.3 M sodium acetate in the presence of linearacrylamide carrier (58 µg/ml), dissolved in water, and in some cases, purified using a Qiagen™ MinElute kit. The cDNAs were then circularized with CircLigase I or II (Epicentre®) according to the manufacturer's instructions and treated with exonuclease I (Epicentre®) according to the manufacturer's instructions to remove any remaining linear cDNA molecules. The circularized cDNAs were relinearized using an Epicentre® uracil DNA excision (UDE) kit according to the manufacturer's instructions with the excision buffer at 0.5× concentration to keep the EDTA concentration low enough for PCR. The reaction products were amplified with Accuprime Pfx polymerase (Invitrogen™) or Flash Phusion® (Finnzymes) according to the manufacturers instruction's using the SOLiD 5' and 3' primers (SOLID 5': 5'-CCACTACGCCTCCGCTTTCCTCTC-TATGGGCAGTCGGTGAT; (SEQ ID NO. 8) SOLID 3': 5'-CTGCCCCGGGTTCCTCATTCTCT/BARCODE/CT-GCTGTACGGCCA AGGCG) (SEQ ID NOs. 9-10) for 15 to 35 cycles of 95° C., 55° C. and 68° C. for 5 sec each. The PCR products were band isolated from a 3% agarose gel (Wizard SV Gel and PCR Clean-Up Kit: Promega®, Madison, Wis.) and either TA cloned (Taq DNA polymerase, TOPO TA cloning kit; Invitrogen™) or cloned into the Zero Blunt® PCR cloning kit (Invitrogen™) for Sanger sequencing with the M13 F(–20) primer or sequenced directly by SOLiD sequencing.

Reverse transcription reactions with the group II intron L1.LtrB RT (LtrA protein) were performed by incubating the purified protein with artificial oligonucleotide substrates (see below) in 20 µl of 450 mM NaCl, 5 mM MgCl$_2$, 20 mM Tris-HCl pH 7.5, 1 mM dithiothreitol (DTT) and 200 µM dNTPs. The reaction components were assembled on ice with substrate added last and incubated at 30° C. for 30 min. Reactions were terminated by phenol-CIA extraction. Portions of the reaction product (3 µl) were added to an equal volume of gel loading buffer II (95% formamide, 18 mM EDTA and 0.025% each of SDS, xylene cyanol, and bromophenol blue (Ambion, Austin, Tex.)), denatured at 98° C. for 7 min, and run in a denaturing 10 or 15% polyacrylamide gel, which was scanned with a PhosphorImager™.

The reactions described in FIG. 4 used L1.LtrB RNA (5'-GUGCGCCCAGAUAGGGUGUUCUCGUUG-GCAAUGGUGUCCAACUUGUGCUGCCAG UGCUCG-AmMO-3') (SEQ ID NO. 11) with annealed primer c (5'-CGAGCACTGGCAGCACAAG/dU/ TGGACACCATTGCCAACGAGAACAC) (SEQ ID NO. 12) and exon 1 DNA (5'-TGTGATTGCAACCCACGTC-GATCGTGAACACATCCATAAC) (SEQ ID NO. 13) or

RNA (5'-UGUGAUUGCAACCCACGUCGAUCGUGAA-CACAUCCAUAAC) (SEQ ID NO. 14).

The reactions described in FIG. 5 used Exon 2 DNA (5'-CATATCATTTTTAATTCTACGAATCTT-TATACTGGCAAAC) (SEQ ID NO. 15) or Exon 2 RNA (5'-CAUAUCAUUUUUAAUUCUACGAAUCU-UUAUACUGGCAAAC) (SEQ ID NO. 16) with annealed primer e2 (5'-CATCTGGCGGCTGTTCTCG/dU/TGGA-CACCATTGCCAACGAGGTTTGCCAGTA TAAAGAT-TCGTAGAATTAA) (SEQ ID NO. 17).

DNA and RNA oligonucleotides were obtained from Integrated DNA Technologies (IDT; Coralville, Iowa) and gel-purified in a denaturing 10% (w/v) polyacrylamide gel by freezing in an Eppendorf tube at −80° C. for 10 min, and then crushing the gel slices and soaking them overnight at 4° C. in 0.5 M $NH_4Cl$, 0.1 M EDTA, 10 mM MOPS, pH 6.5 and 0.1% SDS. The oligonucleotides were separated from gel fragments by using Costar Spin-X centrifuge tube filters, 0.45μm pore size (Corning™ Inc, Lowell, Mass.), then ethanol precipitated in the presence of linear acrylamide carrier (58 μg/ml) and dissolved in nuclease-free water. DNA primers were 5'-end labeled with [$\gamma$-$^{32}$P]-ATP (10 Ci/mmol; Perkin-Elmer) using phage T4 polynucleotide kinase (New England Biolabs®) according to the manufacturer's protocol. For annealing of primers, oligonucleotides were mixed at 20× the concentration used in RT assays, then heated to 82° C. and slowly cooled to 25° C. for 45 min in 1× annealing buffer (100 mM Tris-HCl pH 7.5 and 5 mM EDTA). The efficiency of annealing was assessed by electrophoresis in a non-denaturing 10% polyacrylamide gel containing Tris-borate-EDTA (90 mM Tris, 90 mM boric acid, 2 mM EDTA) at 30° C. (Sambrook et al. 1989).

For cloning and sequencing of cDNAs synthesized with the L1.LtrB RT, the cDNA products were gel-purified from a denaturing 10% (w/v) polyacrylamide gel slices by excising the band, freezing in an Eppendorf tube at −80° C. for 10 min, crushing in the tube, adding 600 μl of 500 mM $NH_4Cl$, 100 μM EDTA, 10 mM MOPS pH 6.5 and 0.1% SDS, and incubating at 4° C. overnight. The oligonucleotide was separated from gel fragments by using Costar Spin-X centrifuge tube filters, 0.45 μm pore size (Corning™ Inc, Lowell, Mass.), ethanol precipitated in the presence of linear acrylamide carrier (58 μg/ml), and dissolved in nuclease-free water. The cDNAs were circularized using CircLigase I or II (Epicentre®), treated with exonuclease I (Epicentre®), and linearized with uracil-DNA excision enzyme mix (Epicentre®), all according to manufacturer's instructions with excision buffer at 0.5× concentration to keep the EDTA concentration low enough for PCR. For the experiment of FIG. 4, the linearized products were PCR amplified by using Phusion® High Fidelity PCR Master Mix with HF buffer (New England Biolabs™, Ipswich, Mass.) with the primers Anchor 6 complement (5'-CTTGTGCTGCCAGTGCTCG) (SEQ ID NO. 18) and Anchor 5 (5'-TGGACACCATTGCCAACGAG) (SEQ ID NO. 19). For the experiment of FIG. 5, the linearized products were PCR amplified similarly with the primers Anchor 4 complement (5'-CGAGAACAGCCGCCAGATG) (SEQ ID NO. 20) and Anchor 5 (see above). PCRs were done in 50 μl of reaction medium Phusion® High Fidelity PCR Master Mix with HF buffer (New England Biolabs™) with the following cycling conditions: 98° C. initial denaturing for 2 min, 25 cycles of 98° C. for 10 see, 60° C. for 10 sec, 72° C. for 5 see, and a final extension at 72° C. for 7 min. PCR products were resolved in a 2% agarose and gel purified with MinElute Gel Extraction Kit (Qiagen®) prior to cloning into the TOPO-TA pCR2.1 vector (Invitrogen™) according to the manufacturer's protocol. Random colonies were picked and the cloned PCR products were amplified by colony PCR using Phusion® High Fidelity PCR Master Mix with HF buffer with primers M13 F(−20) (5'-GTAAAACGACGGC-CAGT) (SEQ ID NO. 21) and M13 R(−26) (5'-CAGGAAA-CAGCTATGAC) (SEQ ID NO. 22), then sequenced using the M13 R(−24) (5'-GGAAACAGCTATGACCATG) (SEQ ID NO. 23) primer.

Example 4

Figure 1:
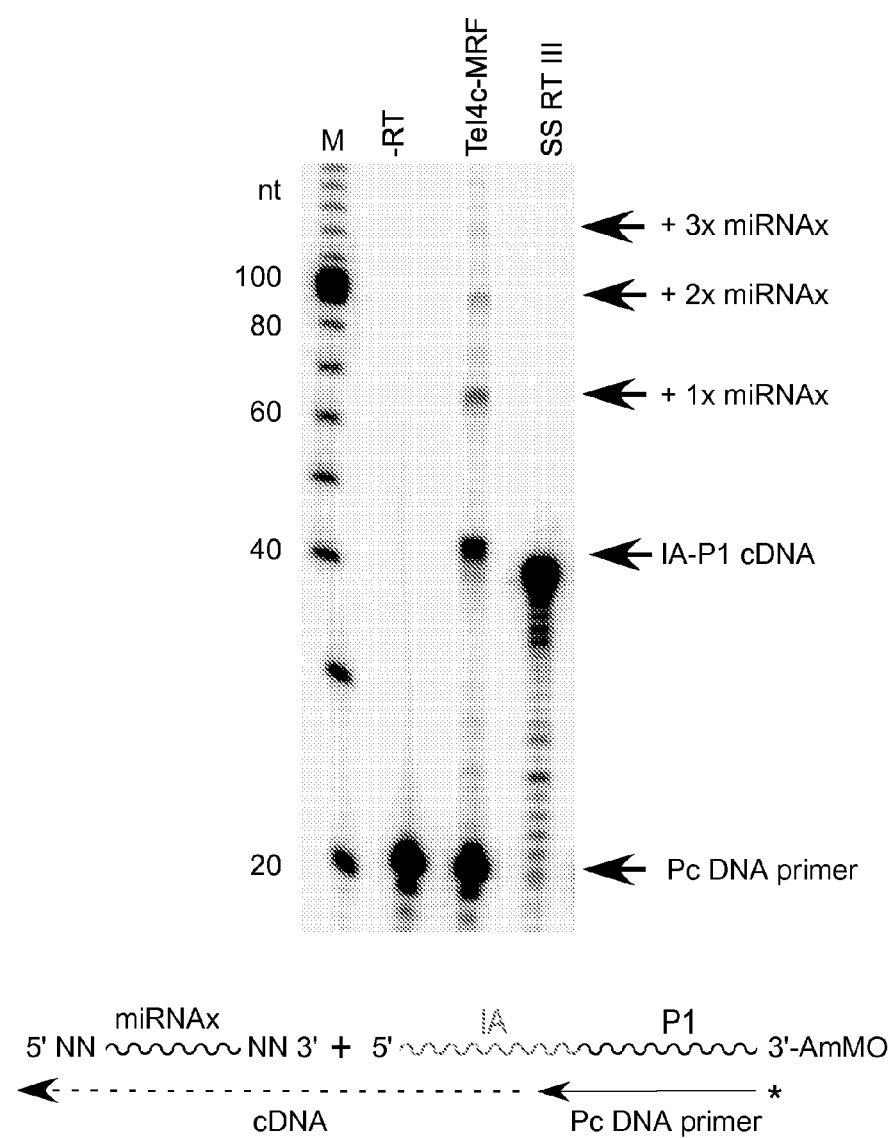
FIG. 1. Comparison of template-switching activities of TeI4c-MRF and Superscript III RTs. IA-P1 RNA/Pc DNA template/primer substrate (50 nM) with 5' $^{32}$P-labeled primer Pc was mixed with an equimolar concentration of miRNAx and reverse transcribed with TeI4c-MRF RT (2 µM) or SuperScript III (SSIII) RT (10 units/µL). The reactions were done under optimal conditions for each enzyme (75 mM KCl, 10 mM MgCl$_2$, 20 mM Tris-HCl-pH 7.5, and 1 mM dNTPs at 60° C. for TeI4c-MRF RT, and 75 mM KCl, 10 mM MgCl$_2$, 40 mM Tris-HCl, pH 8.3, and 1 mM dNTPs at 50° C. for SuperScript III RT). The reactions were started by adding the RT, incubated for 30 min, and stopped by adding EDTA/SDS (0.125 M, 0.05% final), followed by extraction with phenol-chloroform-isoamyl alcohol (25:24:1; phenol-CIA). The products were analyzed in a denaturing 20% polyacrylamide gel, which was scanned with a PhosphorImager™. The -RT control lane shows the IA-P1 RNA/Pc DNA template/primer substrate incubated without RT under the TeI4c-MRF RT reaction conditions. M, $^{32}$P-labeled 10-bp ladder (Invitrogen™) used as size markers. AmMO denotes the aminomodifier at the 3' end of the IA-P1 RNA, * denotes $^{32}$P-label at the 5' end of the primer, and N's denote two randomized nucleotide residues at both the 5' and 3' ends of the miRNAx oligonucleotide used in later experiments to assess biases during template switching.

Analysis of Template Switching and Non-Templated Nucleotide Addition by the Thermostable TeI4c-MRF Group II Intron RT FIG. 1 compares the ability of the thermostable TeI4c-MRF group II intron RT and Superscript III RT to template switch from an RNA template/DNA primer substrate denoted IA-P1 RNA/Pc DNA to the 3' end of a 21-nt RNA oligonucleotide (denoted miRNAx), whose sequence is similar to that of a plant miRNA (*Arabidopsis thaliana* ath mir-173; Park et al. 2002) with two randomized nucleotide residues (N's) at both the 5'- and 3'-ends to assess biases during template switching. The template/primer substrate consists of a 42-nt template RNA (denoted IA-P1 RNA), containing the Internal Adaptor (IA) and P1 sequences for SOLiD next generation sequencing with an annealed 31-nt DNA primer (denoted Pc) complementary to Pt and part of the IA sequence (FIG. 2). The IA-P1 template RNA was synthesized with a 3'-aminomodifier (AmMO; IDT) to impede its being recopied by template switching to its 3' end, and the Pc DNA primer was $^{32}$P-labeled at its 5' end and contains an internal deoxyuridine for subsequent linearization of circularized cDNAs with uracil DNA excision mix (UDE; Epicentre; FIG. 2). The reverse transcription reactions with the TeI4c-MRF and SuperScript III RTs were done under optimal conditions for each enzyme (see legend FIG. 1).

While SuperScript III yields a single predominant product of ~42 nt (IA-Pt cDNA) resulting from extension of the Pc primer to the 5' end of IA-P1 RNA template, the TeI4c-MRF RT yields a similar product plus a series of larger bands of the size expected for template switching linking one, two, or three copies of the 21-nt miRNAx to the IA-P1 adaptor sequence. The major ~42-nt band resulting from termination of cDNA synthesis at the end of the IA-P1 RNA is slightly larger for the TeI4c-MRF RT than for SuperScript III, suggesting that the group II intron RT has a greater propensity to add extra nucleotide residues to the 3' end of the cDNA after it reaches the 5' end of the RNA template. Such extra nucleotide addition is a property of other DNA polymerases and RTs (Clark et al. 1987; Clark 1988, Hu 1993, Patel and Preston 1994, Peliska and Benkovic 1992, Golinelli and Hughes 2002). It is generally termed "non-templated nucleotide addition" or "terminal transferase" activity (Golinelli and Hughes 2002, Andrade et al. 2009) because it occurs at the 3' end of the DNA product strand after the enzyme has reached the 5' end of the template. Herein we refer to it as non-templated nucleotide addition activity or extra nucleotide addition activity.

To clone and sequence the cDNAs synthesized via group II intron RT template switching, the inventors developed the procedure outlined in FIG. 2. After cDNA synthesis with the group II intron RT, the products are incubated with RNase H to digest the RNA template strands, purified in a denaturing 20% polyacrylamide gel, circularized with CircLigase, and digested with exonuclease to remove unligated cDNAs. The circular cDNAs are then relinearized with uracil DNA excision mix at the deoxyuridine residue that had been incorporated into the Pc DNA primer sequence (FIG. 2, bottom), enabling facile amplification using the SOLiD 5' and 3' primers.

The step of gel purification of cDNAs in the procedure of FIG. 2 can be dispensed with for applications that do not require identification of a specific-sized cDNA band. The cDNAs could also be cloned without the use of CircLigase by ligating a second adaptor to the 3' end of the cDNA or by using the non-templated nucleotide addition activity of the RT or another enzyme (e.g., terminal deoxynucleotidyl transferase) to add a homopolymer tail (e.g., poly(dA)), enabling annealing of a second adaptor containing a complementary homopolymer run (e.g., poly(dT)). Additionally, RNase H treatment is optional if the cDNA is gel-purified in a denaturing gel. The circularized cDNA could also be PCR amplified without the uracil-excision linearization step or could be linearized by some other means, such as restriction enzyme digestion at a restriction site incorporated in the oligonucleotide adaptor. In different experiments described below, the PCR products resulting from amplification of the cDNAs were either cloned into a TOPO TA vector or cloned into the Zero Blunt® PCR cloning kit (Invitrogen™) and sequenced by the Sanger method or sequenced directly by next-generation SOLiD sequencing.

FIG. 3 shows sequences of cDNAs generated by template-switching of the TeI4c-MRF RT under the same conditions as FIG. 1. The cDNAs potentially resulting from the first template switch from the IA-P1 RNA/DNA primer substrate to miRNAx and the second template switch to a second molecule of miRNAx were band isolated, cloned using the procedure shown in FIG. 2, and sequenced by the Sanger method with the M13F(–20) primer. The cloning and sequencing of the ~65-nt product confirmed that it resulted from template-switching from the IA-P1 RNA adaptor sequence to the miRNA, thereby linking the adaptor the miRNA sequence. In all cases, the template switch occurred seamlessly without the addition of extra nucleotide residues at the junction of the two RNA sequences. However, 1-15 extra nucleotide residues were added to the 3' end of the cDNA after reaching the 5' end of the miRNA template, with an A-residue added preferentially as the first extra nucleotide. Additionally, the cDNA sequences showed significant biases at the position opposite the 3'-terminal nucleotide residue of the miRNA template: A, 46%; C; 33%; G, 21%; and U, 0%. These biases in the cDNA sequence suggest that the template switch from the template/primer substrate favored miRNAs with a 3' terminal U-residue and strongly disfavored miRNAs with a 3' terminal A-residue.

The cloning and sequencing of the ~85-nt product confirmed that it resulted from two consecutive template switches to the miRNA template, resulting in the IA-P1 adaptor sequence linked to two tandem copies of the miRNA sequence (not shown). Again, attachment of the adaptor sequence occurred seamlessly, with no extra nucleotide residues incorporated at the junctions of either the first or second template switches in 11 clones analyzed. However, extra nucleotide residues were again added to the 3' end of the completed cDNA, with an A-residue added preferentially as the first extra nucleotide, and the initial template switch again showed a strong bias against switching from the IA-P1 RNA to miRNAs with a 3' A-residue (indicated by the lack of T-residues at the position opposite the 3'-terminal miRNA nucleotide in the cDNA sequence (not shown)).

Example 5

Analysis of Template Switching and Non-Templated Nucleotide Addition by the *Lactococcus lactis* L1.LtrB Group II Intron RT (LtrA Protein)

To determine if propensity for template switching and non-templated nucleotide addition are general properties of group II intron RTs, we carried out biochemical assays with the mesophilic *Lactococcus lactis* L1.LtrB group II intron RT. In the experiment shown in FIG. 4A, the initial template/primer substrate consisted of a 60-nt RNA template whose 5' end corresponds to that of the L1.LtrB intron with an annealed 45-nt DNA primer (primer c; denoted Pri c in the Figure). The L1.LtrB RT initiates reverse transcription of the intron RNA template from the annealed DNA primer and extends it to the 5' end of the RNA, where it can then jump to a second 40-nt DNA or RNA template with the nucleotide sequence of ltrB exon 1 (E1 RNA or DNA). The 3' end of the L1.LtrB RNA has an aminomodifier (AmMO) to impede the ability of the RT to switch to a second molecule of the initial template. The reactions were done in reaction medium containing 200 µM dNTPs, 450 mM NaCl, 5 mM $MgCl_2$, 20 mM Tris-HCl pH 7.5, and 1 mM dithiothreitol (DTT), the high salt concentration having been shown previously to be required for optimal activity of the L1.LtrB RT (Saldanha et al. 1999).

Figure 4A:
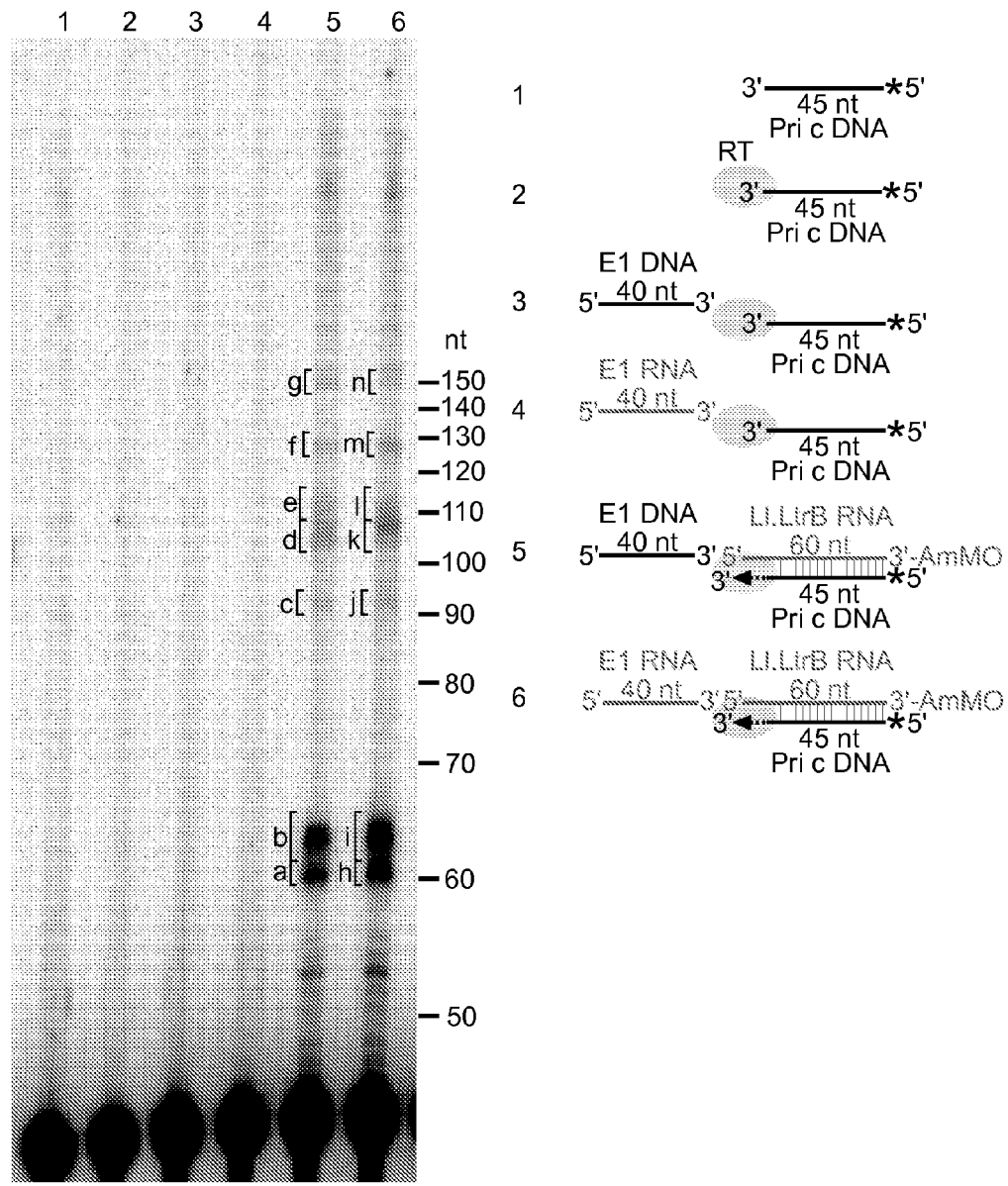
FIG. 4. Non-templated nucleotide addition and template switching by the L1.LtrB group II intron RT using RNA template/DNA primer substrates corresponding to the 5' end of the L1.LtrB intron RNA. (A) Gel assay. The L1.LtrB intron RT (LtrA protein; 40 nM) was incubated with small artificial substrates diagrammed to the right of the gel in reaction medium containing 200 µM dNTPs, 450 mM NaCl, 5 mM MgCl$_2$, 20 mM Tris-HCl pH 7.5, and 1 mM dithiothreitol (DTT) for 30 min at 30° C. The artificial substrates were 44 nM 5'-$^{32}$P-labeled DNA primer c (Pri c; 45 nt) by itself or annealed to 40 nM L1.LtrB RNA (60 nt) plus 40 nM exon 1 (E1; 40 nt) DNA or RNA. After incubation, the reaction was terminated by phenol-CIA extraction, and the products were analyzed in a denaturing 15% polyacrylamide gel, which was scanned using a PhosphorImager™. Lanes (1) and (2) $^{32}$P-labeled Pri c incubated without and with LtrA, respectively.
FIG. 4B discloses SEQ ID NOS 54-61, 61, 61, 61, 61-62, 62-63, 61 and 25, respectively, in order of appearance.
FIG. 4C discloses SEQ ID NOS 64, 55, 57, 65, 58, 66, 59, 67-68, 60-61, 69, 62, 70-72, 72 and 72-74, respectively, in order of appearance. Products obtained from the indicated gel bands in lanes 5 and 6, respectively, resulting from extension of primer c to the 5' end of the L1.LtrB RNA in the L1.LtrB RNA template/DNA primer c substrate and subsequent template switching to exon 1 DNA or RNA. Mutant nucleotide residues in the DNA product sequences are shown in lower case letters, and extra nucleotide residues inserted at template-switching junctions or the 3' ends of cDNAs are shown in bold lower-case letters. Portions of the DNA product sequences not shown in the figure included one G to A transition for exon 1 DNA products and two A to G transitions for exon 1 RNA products. Numbers to the right indicate the frequency of each sequence. * denotes $^{32}$P-label at the 5' end of primer c.

FIG. 4A lanes 5 and 6 show that the L1.LtrB RT efficiently extends the primer to the end of the intron RNA template, yielding major labeled products of ~60-nt, the size expected for extension of the Pri c DNA primer to the end of the initial L1.LtrB RNA template, along with smaller amounts of larger products of the size expected for template-switching to the exon I DNA or RNA (100 nt) or to a second molecule of L1.LtrB RNA despite the aminomodifier (120 nt). The ~60-nt product was resolved as a doublet, presumably reflecting non-templated nucleotide addition to the 3' end of the initial cDNA. The control lanes (lanes 1-4) show that such labeled products were not detected for primer c by itself or for primer c incubated with the RT by itself or in the presence of the exon 1 RNA or DNA (lanes 1-4).

Cloning and sequencing of cDNA products is summarized in FIGS. 4B and C. The sequencing confirmed that the major ~60-nt products (bands a and b in lane 5 and h and i in lanes 6) correspond to cDNAs extending to or near the 5' end of the L1.LtrB RNA, with the doublet reflecting the addition of extra nucleotides nucleotide residues, mostly A-residues, to the 3' end of the cDNA upon reaching the end of the RNA template (FIGS. 4B and C).

The larger bands (band c-g in lane 5 and h-n in lane 6) contain products generated by template switching from the 5' end of the intron to the 3' end of exon 1 DNA or RNA (FIGS. 4B and C), as well as products generated by template switching to internal regions or to the 3' end of L1.LtrB RNA despite the aminomodifier (not shown). Bands c, d and e contain products generated by template switching to exon 1 DNA (FIG. 4B). Bands j, k and l contain products generated by template switching to exon 1 RNA (FIG. 4C). Most (70%) of the template switches to exon 1 DNA occurred seamlessly, but extra nucleotide residues, mostly A-residues, were found at some (30%) of the template-switching junctions, as well as at the 3' ends of most (92%) of the DNA products. We found 61% of the template-switching junctions to exon I RNA had extra nucleotide residues and 44% of the 3' ends of cDNAs had extra nucleotide residues, mostly A-residues in both cases. We found 48% of the template-switching junctions to L1.LtrB RNA had extra nucleotide residues and 50% of the 3' ends of cDNAs had extra nucleotide residues, mostly A-residues in both cases (not shown). In some cases, the L1.LtrB RT adds runs of A-residues. Band g contains products generated by two consecutive template switches to exon 1 DNA. Band n contains products generated by two consecutive template switches to exon 1 RNA. Bands d, f, j, k, and m contain products generated by template switching to L1.LtrB RNA. Band m also contains products generated by two consecutive template switches to L1.LtrB RNA. Band k also contains products generated by two consecutive template switches: first to exon I RNA followed by L1.LtrB RNA. The products with multiple template-switches have characteristics similar to the products with a single template switch, including non-templated nucleotide residues, A-residues in most cases, incorporated at some of the template-switching junctions and at the 3' ends of most cDNAs. The propensity to add extra non-templated nucleotide residues between template switches is greater for the L1.LtrB RT than for the TeI4c-MRF RT in these experiments, reflecting either differences in the RT or experimental conditions. Notably, the experiment of FIG. 4 shows that template switching by the group II intron RT can occur regardless of whether the second template is RNA or DNA.

Figure 5A:
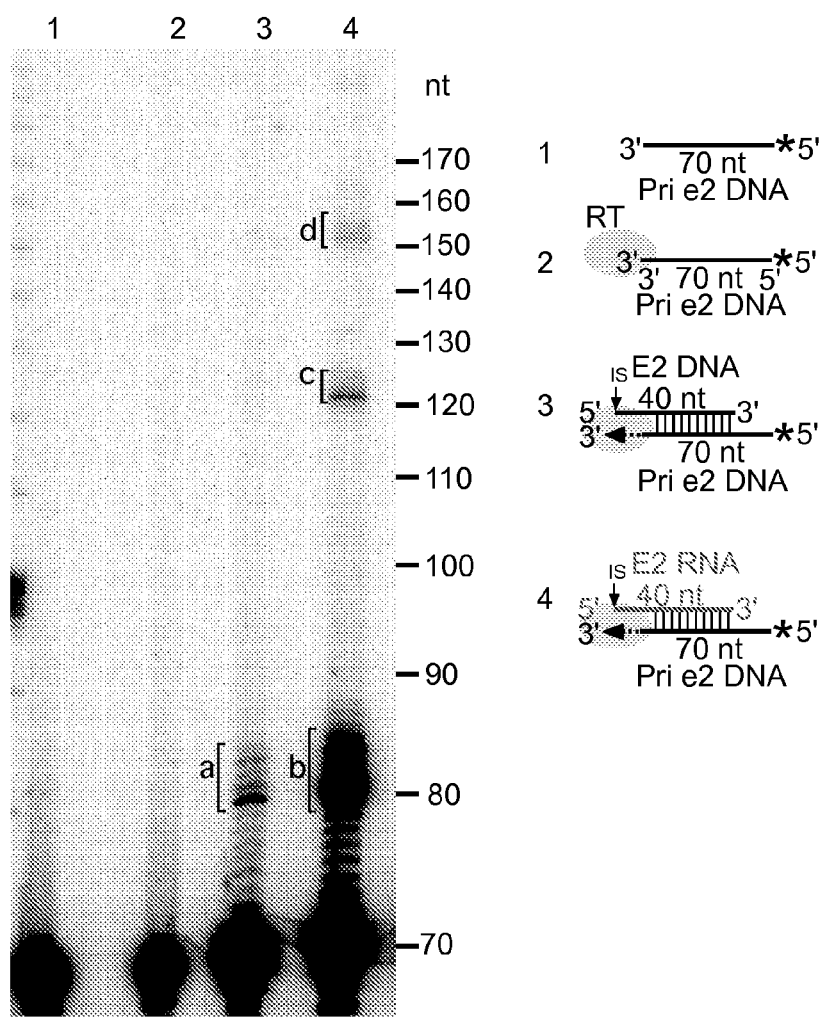
FIG. 5. Non-templated nucleotide addition and template switching by the L1.LtrB group II intron RT using RNA template/DNA primer substrates corresponding to the 3' L1.LtrB intron-exon 2 integration junction. (A) Gel assays. The L1.LtrB RT (LtrA protein; 40 nM) was incubated with small artificial substrates diagrammed to the right of the gel in reaction medium containing 200 μM dNTPs, 450 mM NaCl, 5 mM MgCl$_2$, 20 mM Tris-HCl, pH 7.5, 1 mM dithiothreitol for 30 min at 30° C. The artificial substrates were 44 nM 5'-$^{32}$P-labeled primer e2 (Pri e2; 70 nt) by itself or annealed to 40 nM E2 RNA or DNA (40 nt). The reaction was terminated by phenol-CIA extraction, and the products were analyzed in a denaturing 10% polyacrylamide gel, which was scanned using a PhosphorImager™. Lanes (1) and (2) $^{32}$P-labeled Pri e2 DNA incubated without and with LtrA, respectively; (3) and (4) LtrA incubated with E2 DNA or RNA template with annealed $^{32}$P-labeled Pri e2, respectively. In the schematics, the L1.LtrB RT is shown as a gray oval, and the direction of DNA synthesis is indicated by a dotted arrow. IS indicates the intron-insertion site. The numbers to the right of the gel indicate the position of the 5'-$^{32}$P-labeled 10-bp ladder (Invitrogen™). (B) Sequences of cDNA products.
FIG. 5B discloses SEQ ID NOS 75-76, 76-92, 87-88 and 93-116, respectively, in order of appearance. The bands indicated in the gel (a-d) were excised, cloned, and sequenced. The template and expected DNA product sequences (boxed) are shown above each set of experimentally determined DNA product sequences. Mutant nucleotide residues in DNA product sequences are shown in lower case letters, and extra nucleotide residues inserted at template-switching junctions or the 3' ends of cDNAs are shown in bold lower-case letters. Numbers to the right indicate the frequency of each sequence. * denotes $^{32}$P-label at the 5' end of the primer.

FIG. 5 shows a second set of biochemical assays with the L1.LtrB RT using different template/primer substrates corresponding to ltrB exon 2 (E2) DNA or RNA with an annealed DNA primer (e2). As expected from previous work (Smith et al. 2005), the L1.LtrB RT displayed high RT activity on the RNA template, but only low DNA-dependent DNA polymerase activity on the DNA template (FIG. 5A, lanes 3 and 4). The majority of products obtained with the RNA template extend beyond the 10-nt 5' overhang (FIG. 5A, lane 4), and cloning and sequencing of these cDNAs revealed extra nucleotide residues, now mostly C-residues including homopolymer runs of up to 7 C-residues, added to the 3' end of the cDNA (FIG. 5B). Sequencing showed that the larger products in FIG. 5B lane 4 were generated by template switching from the initial E2 RNA to a second and sometimes a third molecule of E2 RNA, which in this experiment had no 3' amino-modifier to impede template switching (FIG. 5B). In these cases, extra nucleotide residues, again mostly C-residues, were found at the junctions between the template switches and at the 3' end of the cDNA. These findings show that the specificity of non-templated nucleotide addition by group II intron RTs can differ for different template/primer substrates and cDNAs. Similar findings have been made for other RTs and DNA polymerases and attributed to differences in the terminal nucleotide residues of the DNA product strand, which could, for example, engage in base-stacking interactions that favor some incoming nucleotides over others (Hu 1993; Magnuson et al. 1996; Golinelli and Hughes 2002). The ability of group II intron RTs to add extra nucleotide residues, including homopolymer runs, to the 3' ends of cDNA may be used for cDNA cloning—e.g., into vectors that contain a complementary nucleotide residue overhang or by enabling annealing of a second adaptor with a complementary homopolymer sequence.

Example 6

Effect on Changing Reaction Conditions on Non-Templated Nucleotide Addition by a Group II Intron RT Although potentially useful, the ability of group II intron RTs to add extra nucleotide residues to the 3' ends of cDNAs could be deleterious for some applications that require accurate sizing of the cDNAs (e.g., capillary electrophoresis) and could contribute to biases in template switching by introducing complementarity between the 3' end of the cDNA and 3' end of the new RNA template. In the experiment of FIG. 3, for example, the preferential addition of an extra A-residue to the 3' end of the cDNA by the TeI4c-MRF RT could bias it to template switch to miRNAs with a complementary 3' U residue and disfavor miRNAs with a clashing 3' A residue. Although template switching by group II intron RTs may also occur without base pairing between the cDNA and new RNA template, the potential for base pairing or clashes with extra nucleotide residues added to the 3' end of the cDNA could strongly favor switching to some templates over others. Thus, time was spent to find conditions in which the extent of non-templated nucleotide addition to the 3' end of cDNA could be minimized or controlled.

Figure 6:
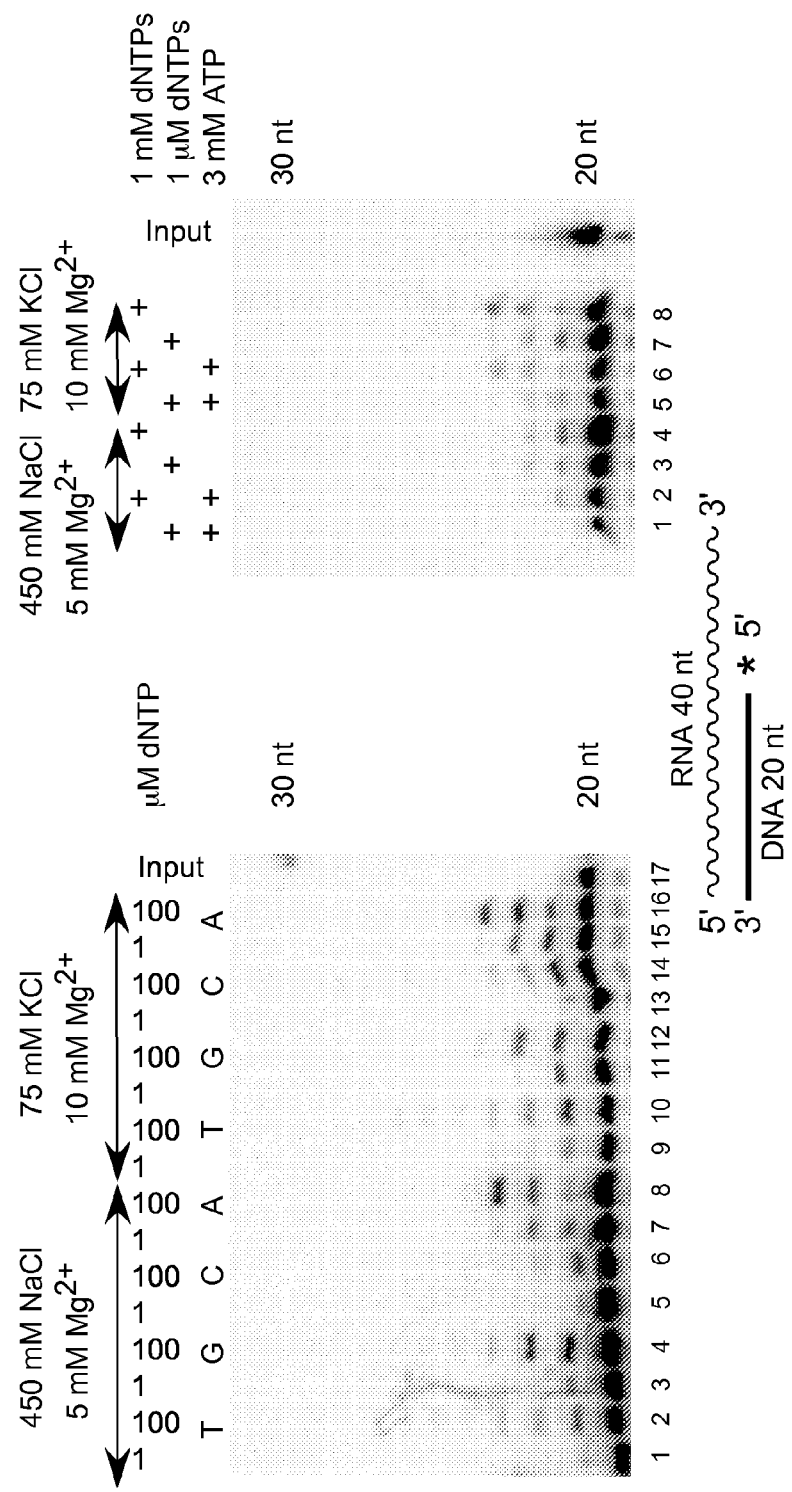
FIG. 6. Assays of non-templated nucleotide addition to blunt-end RNA template/DNA primer substrates. The RNA template/DNA primer substrate has a blunt end mimicking a cDNA fully extended to the 5' end of an RNA template (40-nt RNA template 5'-GUGCGCCCAGAUAGGGUG-UUAAGUCAAGUA-3' (SEQ ID NO: 1); 20-nt DNA primer 5'-AACACCCTATCTGGGCGCAC-3' (SEQ ID NO: 2)). TeI4c-MRF RT (2 μM) was incubated with the RNA template/DNA primer substrate (100 nM) for 10 min at 60° C. in reaction media containing 450 mM NaCl, 5 mM MgCl$_2$, 20 mM Tris-HCl, pH 7.5 or 75 mM KCl, 10 mM MgCl$_2$, 20 mM Tris-HCl, pH 7.5 and 1 or 100 μM dATP, dCTP, dGTP, or dTTP (gel to the left), or 1 μM or 1 mM of all four dNTPs and 3 mM ATP (gel to the right), as indicated above each lane. After terminating the reaction by adding 125 mM EDTA and 0.05% SDS followed by phenol-CIA extraction, the products were analyzed in a denaturing 20% polyacrylamide gel, which was scanned with a PhosphorImager™. The positions of 10-bp ladder markers (Invitrogen™) are shown to the right of the gels. * denotes $^{32}$P-label at the 5' end of the primer.

To find such conditions, the assay shown in FIG. 6, which employs an RNA template/DNA primer substrate with a blunt 5' RNA/3' DNA end that mimics a cDNA primer fully extended to the 5' end of the RNA template, was used. This DNA substrate was incubated with the TeI4c-MRF RT under different reaction conditions in the presence of different concentrations of each of the four dNTPs. The results showed that (i) the order of preference for addition of non-templated nucleotide residues to the 3' end of the DNA strand by the TeI4c-MRF RT for this template/primer substrate RNA was A>G>C>T; (ii) non-templated nucleotide addition could be decreased by a combination of higher monovalent salt and lower $Mg^{2+}$ concentrations (e.g., 450 mM NaCl and 5 mM $Mg^{2+}$) and lower dNTP concentrations (e.g., 1 µM rather than 1 mM). It was also found that non-templated nucleotide addition could be decreased by ATP, which was found previously to decrease non-templated nucleotide addition by HIV-1 RT (Golinelli and Hughes 2002). In other experiments, the inventors also found that non-templated nucleotide addition by group II intron RTs is a relatively slow reaction compared to cDNA synthesis and thus could be decreased by carrying out the reaction for short times. Low pH has been reported to decrease non-templated nucleotide addition by HIV1 RT (Golinelli and Hughes 2002) and may similarly decrease non-templated nucleotide addition by group II intron RTs. The strong dependence of non-templated nucleotide addition upon dNTP concentrations suggests that by using different ratios of dNTPs, it may be possible to favor the addition of one specific dNTP, resulting in homopolymer runs, such as poly (A) or poly(C), that would enable annealing with a complementary nucleotide for cDNA cloning and sequencing. The group II intron RTs could also be used in a separate reaction step with a single dNTP to add a desired tail to the 3' end of DNAs.

Example 7 cDNA Cloning and Sequencing by Template-Switching Under Reaction Conditions that Minimize Non-Templated Nucleotide Addition Having identified reaction conditions that minimize non-templated nucleotide addition by the group II intron RT, the miRNA cloning and sequencing experiment in which the TeI4c-MRF RT template switches from the IA-P1 RNA/Pc DNA template-primer substrate to the 21-nt miRNA with two randomized nucleotides at both the 5' and 3' ends was repeated, but now under reaction conditions intended to decrease non-templated nucleotide addition (450 mM NaCl, 5 mM $MgCl_2$, 20 mM Tris-HCl, pH 7.5 for 10 min). The resulting cDNAs were cloned using the protocol of FIG. 2 and analyzed by both Sanger (not shown) and next-generation SOLiD sequencing, using a concentration of 1 mM dNTPs.

FIG. 7 shows the 20 most abundant sequences among 2,239,072 high-quality reads obtained by SOLiD sequencing. Among the 2,239,072 high-quality reads, 49% had one copy of miRNAx and 51% had two tandem miRNAx sequences reflecting a second template switch to another miRNAx template. The ratio of miRNAx monomer to dimer reads could be increased by more stringent gel purification of the initial cDNA product prior to sequencing. The sequences confirmed that the modified reaction conditions decreased non-templated nucleotide addition to the 3' end of the cDNAs (FIG. 7). Among the cDNAs analyzed by Sanger sequencing, only 33% had an extra 3'-nucleotide residue, most frequently a single A-residue (not shown). For SOLiD sequencing, among 975,020 high-quality reads with miRNAx monomer sequence linked to P2 sequence, 50% had one or more extra 3'-nucleotide residue, most frequently a single A-residue (244,877 reads), and among 1,138,636 high-quality reads of miRNAx dimers, 48% had one or more extra 3'-nucleotide residues, again most frequently a single A-residue (255,257 reads; not shown). The cDNA sequences, however, still showed a strong bias at the position opposite the 3'-terminal nucleotide residue of the miRNAx template (A, 75%; C, 8%, G, 9%; T; 8% in the cDNA sequence based on 974,276 of the high-quality miRNAx monomer reads (see above) in which this position could be read unambiguously), while no significant bias was discerned at the randomized position opposite the penultimate nucleotide residue of the RNA template. The bias seen opposite the 3'-terminal template position is consistent with a model in which template switching occurred preferentially to miRNAx molecules with a 3' U-residue that could base pair with the non-templated A-residue added preferentially at the 3' end of the cDNA.

Example 8

Figure 8:
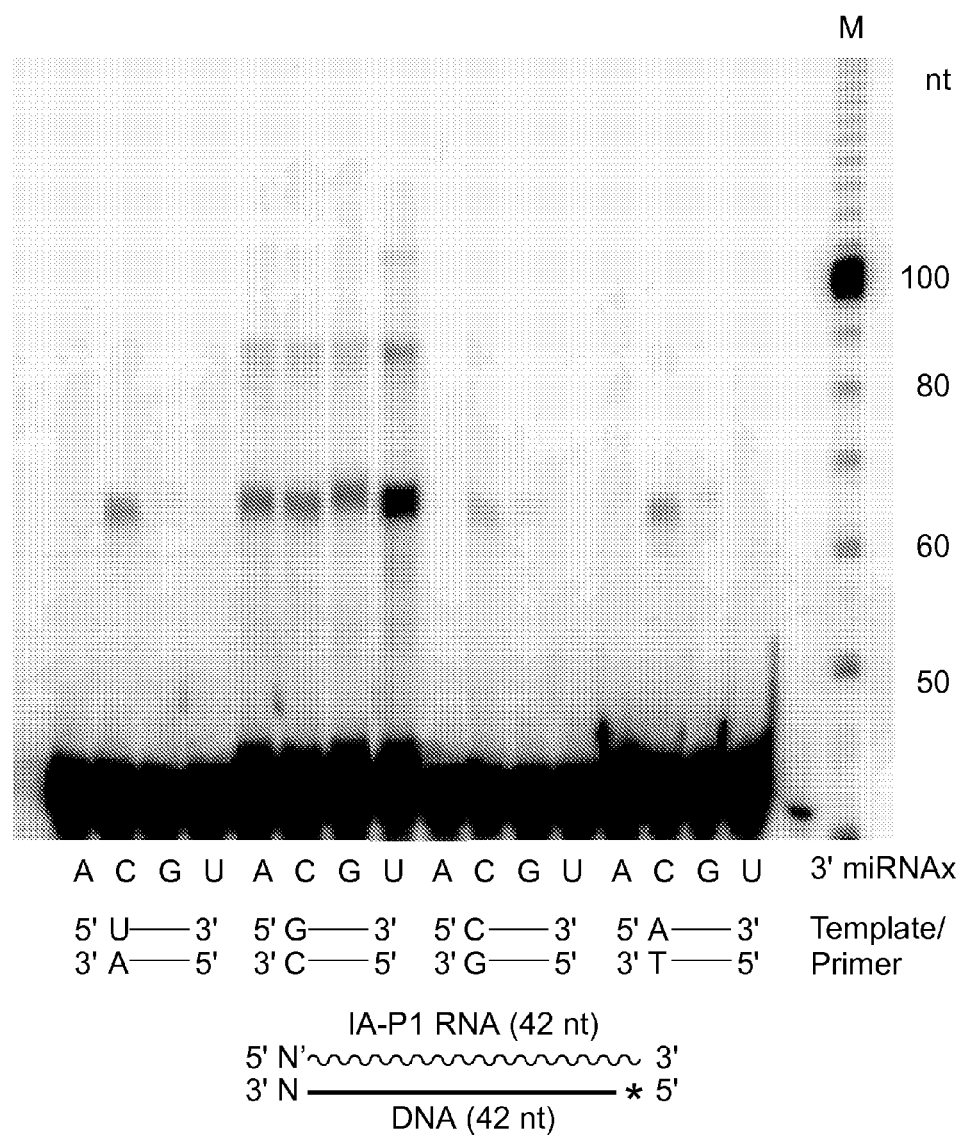
FIG. 8. Template-switching from blunt-end RNA template/DNA primer substrates with different terminal base pairs. $^{32}$P-labeled blunt end RNA template/DNA primer substrates (42-nt IA/P1 RNA template annealed to a complementary 42-nt DNA) with each of the four possible base pairs at the 5' RNA/3' DNA end were used to template switch to miRNAx's, whose 3' terminal nucleotide residue was either A, C, G, or U. The reverse transcription reactions were done in 450 mM NaCl, 5 mM MgCl$_2$, 20 mM Tris-HCl, pH 7.5 with 1 mM dNTPs for 15 min at 60° C. The reactions were initiated by adding the RT and terminated by adding 125 mM EDTA and 0.05% SDS. After phenol-CIA extraction, the products were analyzed in a denaturing 20% polyacrylamide gel, which was scanned with a PhosphorImager™. M, $^{32}$P-labeled 10-bp ladder (Invitrogen™) used as size markers. * denotes $^{32}$P-label at the 5' end of the primer. Based on quantitation of radioactivity in the template-switching product bands normalized for the amount of radioactivity in each gel lane, the percentage of template-switching events from the 5'G RNA/3'C DNA substrate to RNAs with different 3'-terminal nucleotide residues was A, 16%; C, 15%; G, 19%, and U, 50%. The other three blunt-end substrates show preferences for template switching to RNAs with a 3' C-residue.

Minimization of Template-Switching Bias by Use of Different RNA Template/DNA Primer Substrates Other approaches for reducing template-switching biases caused by non-templated nucleotide addition were explored. In one approach, the inventors tested template-switching from blunt-ended RNA/DNA template-primer substrates with different terminal base pairs, mimicking the structure when the cDNA reaches the end of the initial RNA template. FIG. 8 shows gel analysis of template switching from blunt-ended substrates ending in each of the four possible 5' RNA/3' DNA base pairs to miRNAx oligonucleotides with different 3'-terminal nucleotides. By quantifying the band intensity of the template-switching products and normalizing for the amount of radioactivity in each lane, an estimate of percentage of template-switches that occurred to RNAs ending in each of the four nucleotide residues was obtained. Although RNA template/DNA primer substrates ending in U/A, C/G or A/T base pairs all showed preferences for template switching to an miRNAx with a 3' C residue, an RNA template/DNA primer substrate ending with a G/C base pair template switched efficiently to miRNAxs ending with all four nucleotide residues, albeit with some preference for the miRNAx ending with a 3' U residue (U, 43-59%; G, 29-30%; C, 17-19%; and A, 4-12% in three separate experiments). Thus, the use of RNA template/DNA primer substrates with different geometries and nucleotide sequences, such as blunt-end RNA template/DNA primer substrates ending with a G/C base pair, may be used to minimize template-switching biases.

FIG. 9A shows a second approach using a set of IA-P1 RNA template/Pc DNA primer substrates with different 3' overhangs of the priming strand, mimicking the structure expected for non-templated addition of one nucleotide residue to the 3' end of the cDNA. The results showed that these template/primer substrates favored initiation on the RNA template having a complementary 3'-nucleotide residue, as expected, but could still template switch to RNAs with other 3'-terminal nucleotides to some extent. Thus, a template/primer substrate with a 3' A overhang showed a strong preference for template switching to a miRNAx with a complementary 3' U residue; a template/primer substrate with a 3' C overhang template switched efficiently to a miRNAx with a complementary 3' G-residue as well as to a miRNAx with a non-complementary 3' C-residue; a template/primer substrate with a 3'G overhang template switched efficiently to a miRNAx with a complementary 3' C-residue, as well as to a miRNA with a non-complementary 3' G-residue; and a template/primer substrate with a 3' T overhang template switched efficiently to a miRNAx with a complementary 3'A-residue and somewhat less efficiently to a miRNAx with a 3' G-residue, possibly reflecting formation of a TG base pair. In some cases template switching to an RNA with a non-complementary 3' nucleotide residue (−1 position) could reflect base pairing to the nucleotide residue at the −2 or −3 positions (e.g., the primer with a 3' G overhang could be initiating by base pairing with the C-residue at the −3 position of the miRNA template, skipping the two terminal nucleotide residues). Although retroviral RTs can template-switch by using complementarity between non-templated nucleotides added by the RT and the 3' end of new RNA template, at least two base pairs one of which must be a relatively stable GC or CG pair are required for this reaction (Oz-Gleenberg et al. 2011). The template-switching reaction of the TeI4c-MRF RT is novel because only a single base pair of any type is sufficient to promote template switching even at 60° C., the operational temperature of the TeI4c-MRF RT.

Importantly, a mixture of the template/primers substrates with different 3' overhangs showed much decreased bias for different templates. For example, in three separate experiments, an equimolar mixture of template/primer substrates with each of the four possible 3' overhangs switched to miRNAs with different 3'-nucleotide residues as follows: A, 15-27%; C, 28-30%; G, 28-30%; and U, 16-27%; calculated as percentage of the total number of template switches after normalizing for the total radioactivity in each gel lane. Thus, a mixture containing an appropriate ratio of RNA template/DNA primer substrates with different 3' DNA overhangs could be used to decrease template-switching biases for cDNA synthesis and cloning of RNAs of unknown sequence. Conversely, an RNA template/DNA primer substrate with a specific 3' DNA overhang could be used separately to favor amplification of specific RNAs of known sequence Further characterization showed that the group II intron RT template-switching reaction: (i) is inhibited by a 3' phosphate, which would result from conventional RNase- or alkali-cleavage, but restored by 3' phosphate removal; (ii) occurs to DNA as well as RNA, indicating that a 2'OH group on the 3'-terminal nucleotide is not required (FIG. 9B). Thus, in addition to miRNA cloning and sequencing, group II intron RT template switching should be useful for the cloning and sequencing of protein-bound RNA fragments generated by RNase digestion in procedures, such as HITS-CLIP/CRAC or ribosome profiling (Polidoros et al. 2006, Holton & Graham 1991, Granneman et al. 2009, Zhang & Darnell 2011, Ingolia et al. 2009); and perhaps in the construction of DNAseq libraries.

Example 9

Template Switching Using an Additional Group II Intron RT and RNA/DNA or DNA/DNA Template/Primer Substrates Template switching from 3'-overhang substrates was demonstrated using the GsI-IIC-MRF group II intron, as shown in FIG. 10. This figure demonstrates the use of template switching to link a primer with an miRNA sequence, and more generally shows that a third group II RT, GsI-IIC-MRF, belonging to a different structural subclasses (subgroup IIC) carries out the same template switching reaction as the L1.LtrB and TeI4c-MRF RTs, which belong to subgroups IIA and IIB, respectively. Another example of template switching is provided by FIG. 11, which shows template switching using the TeI4c-MRF RT from initial RNA/DNA or DNA/DNA template/primer substrates. This figure demonstrates that either type of template/primer substrate is suitable for carrying out a template switching, although the RNA/DNA template primer substrate is more efficient.

Example 10

Use of Group II Intron RT Template-Switching for miRNA Cloning and Sequencing To assess its utility for library construction, group II intron RT template switching and two commercial kits (Applied Biosystems™ and New England BioLabs™) employing conventional RNA-ligation methods were used to generate libraries for SOLiD sequencing of a reference set consisting of 963 equimolar miRNAs. The inventors then compared the library abundance of 898 of the miRNAs with uniquely identifiable core sequences. The plots show that the two libraries prepared by TeI4c-MRF RT template switching from template-primer substrates with different ratios of 3' overhangs (TS1 and TS2) have more uniform distributions of miRNA sequences (flatter lines) than those prepared by either commercial kit (FIG. 12A). Analysis of outliers identified nine miRNAs that were underrepresented in all libraries, but otherwise little overlap between the miRNAs that were under- or overrepresented by the different methods (FIGS. 12B and C, respectively). FIG. 13 shows that the representation of miRNAs with different 3' terminal nucleotides in the cDNA libraries generated by group II intron RT template switching can be adjusted by using template/primer substrates with different ratios of A, C, G, or T 3' overhangs.

Collectively, the foregoing results demonstrate general methods for preparing a DNA copy of a target polynucleotide using template switching by mixing a double stranded template/primer substrate that consists of a DNA primer oligonucleotide associated with a complementary oligonucleotide template strand with a target polynucleotide in a reaction medium and adding a suitable amount of a group II intron reverse transcriptase to the reaction medium to extend the DNA primer oligonucleotide from its 3' end to provide a DNA copy polynucleotide that includes a complementary target DNA polynucleotide that is synthesized using the target polynucleotide as a template.

The results also demonstrate methods of preparing a DNA copy of a target polynucleotide using template switching by mixing a double stranded template/primer substrate with a target polynucleotide in a reaction medium and adding a suitable amount of a non-retroviral reverse transcriptase to the reaction medium to extend the DNA primer oligonucleotide from its 3' end to provide a DNA copy polynucleotide that includes a complementary target DNA polynucleotide that is synthesized using the target polynucleotide as a template. In this embodiment, the DNA primer oligonucleotide has a blunt end wherein the 3' end of the of the DNA primer oligonucleotide is directly aligned with the 5' end of the complementary oligonucleotide template strand, or an overhanging end wherein the 3' end of the DNA primer oligonucleotide extends 1 nucleotide beyond the 5' end of the complementary oligonucleotide template strand.

The results also demonstrate a method of adding additional nucleotides to a DNA primer oligonucleotide that involves adding a suitable amount of a non-retroviral reverse transcriptase to a reaction medium that includes a double stranded template/primer substrate in which the group II intron adds 1-15 additional non-complementary nucleotides at the 3' end of the DNA primer oligonucleotide

REFERENCES

Andrade P, Martin M J, Juárez R, López de Saro F, Blanco L (2009). Limited terminal transferase in human DNA polymerase mu defines the required balance between accuracy and efficiency in NHEJ. Proc Natl Acad Sci USA 106: 16203-08.

Ausubel F M, Brent R, Kingston R E, Moore, D D (eds). (1999 and preceeding editions) Short Protocols in Molecular Biology: A Compendium of Methods from Current Protocols in Molecular Biology. John Wiley & Sons (New York, N.Y.)

Bartlett J M, Stirling D (2003). A short history of the polymerase chain reaction. Methods Mol Biol 226:3-6.

Bibillo A, Eickbush T H (2002). The reverse transcriptase of the R2 non-LTR retrotransposon: continuous synthesis of cDNA on non-continuous RNA templates. *J Mol Biol* 316: 459-473.

Bibillo A, Eickbush T H (2004). End-to-end template jumping by the reverse transcriptase encoded by the R2 retrotransposon. J Biol Chem 15:14945-53.

Blocker F J H, Mohr G, Conlan L H, Qi L, Belfort M, Lambowitz A M (2005). Domain structure and three-dimensional model of a group II intron-encoded reverse transcriptase. RNA 11:14-28.

Candales M A, Duong A, Hood KS, Li T, Neufeld RAE, Sun R, McNeil BA, Wu L, Jarding AM, Zimmerly S (2012). Database of bacterial group II introns. Nucleic Acids, D187-190 doi:10.1093/nar/gkr1043.

Chen B, Lambowitz A M (1997). De novo and DNA primer-mediated initiation of cDNA synthesis by the Mauriceville retroplasmid reverse transcriptase involve recognition of a 3' CCA sequence. J Mol Biol 3:311-32.

Chen, H, & Boutros, P C (2011). VennDiagram: a package for the generation of highly-customizable Venn and Euler diagrams in R. BMC Bioinformatics 12:35, doi:10.1186/1471-2105-12-35.

Clark J M (1988). Novel non-templated nucleotide addition reactions catalyzed by procaryotic and eucaryotic DNA polymerases. Nucl Acids Res 16:9677-86.

Clark J M, Joyce C M, Beardsley G P (1987). Novel blunt-end addition reactions catalyzed by DNA polymerase I of *Escherichia coli*. J Mol Biol 198:123-7.

Dai L, Toor N, Olson R, Keeping A, Zimmerly S. (2003). Database for mobile group II introns. Nucleic Acids Research 31:424-26.

England T E, Uhlenbeck O C (1978). Enzymatic oligoribonucleotide synthesis with T4 RNA ligase. Biochemistry 17:2069-76.

Golinelli M P, Hughes S H (2002). Nontemplated base addition by HIV-1 RT can induce nonspecific strand transfer in vitro. Biochemistry 41:5894-906.

Granneman S, Kudla G, Petfalski E, Tollervey D (2009). Identification of protein binding sites on U3 snoRNA and pre-rRNA by UV cross-linking and high-throughput analysis of cDNAs. Proc Natl Acad Sci USA 106:9613-8.

Holton, T A & Graham, M W (1991). A simple and efficient method for direct cloning of PCR products using ddT-tailed vectors. Nucleic Acids Res 19:1156.

Hu G (1993). DNA polymerase-catalyzed addition of non-templated extra nucleotides to the 3' end of a DNA fragment. DNA Cell Biol 12:763-70.

Ingolia N T, Ghaemmaghami S, Newman J R, Weissman J S (2009). Genome-wide analysis in vivo of translation with nucleotide resolution using ribosome profiling. Science 324:218-23.

Kennell, J C. Wang, H & Lambowitz, A M (1994). The Mauriceville plasmid of *Neurospora* spp. uses novel mechanisms for initiating reverse transcription in vivo. Mol Cell Biol 14:3094-3107.

Kojima, K K & Kanehisa, M (2008). Systematic survey for novel types of prokaryotic retroelements based on gene neighborhood and protein architecture. Mol Biol Evol 25:1395-1404.

König J, Zarnack K, Rot G, Curk T, Kayikci M, Zupan B, Turner D J, Luscombe N M, Ule J (2010). iCLIP reveals the function of hnRNP particles in splicing at individual nucleotide resolution. Nature Struct & Mol Biol 17:909-15.

Kristelly R, Earnest B T, Krishnamoorthy L, Tesmer J J. (2003). Preliminary structure analysis of the DH/PH domains of leukemia-associated RhoGEF. Acta Crystallog sect D 59:1859-62.

Lambowitz A M, Zimmerly S (2010). Group II introns: mobile ribozymes that invade DNA. In: *RNA Worlds: From Life's Origins to Diversity in Gene Regulation* (R. F. Gesteland, T. R. Cech, and J. F. Atkins, Editors), Cold Spring Harbor Perspect Biol 1:a003616.

Lamm A T, Stadler M R, Zhang H, Gent J I, and Fire, A Z (2011). Multimodal RNA-seq using single-strand, double-strand, and CircLigase-based capture yields a refined and extended description of the *C. elegans* transcriptome. Genome Research 1:1-11.

Lau N C, Lim L P, Weinstein, E G, Bartel D P (2001). An abundant class of tiny RNAs with probably regulatory roles in *Caenorhabditis elegans*. Science 294:858-62.

Levesque-Sergerie J P, Duquette M, Thibault C, Delbecchi L, Bissonnette N (2007). Detection limits of several commercial reverse transcriptase enzymes: impact on the low- and high-abundance transcript levels assessed by quantitative RT-PCR. BMC Mol Biol 8:93.

Levin J Z, Yassour M, Adiconis X, Nusbaum C, Thompson D A, Friedman N, Gnirke A, Regev A (2010). Comprehensive comparative analysis of strand-specific RNA sequencing methods. Nature Methods 7:709-15.

Linsen S E V, de Wit E, Janssens G, Heater S, Chapman L, Parkin R K, Fritz B, Wyman S K, de Bruijn E, Voest E E, Kuersten S, Tewari M & Cuppen E (2009). Limitations and possibilities of small RNA digital gene expression profiling. Nature Methods 6:474-476.

Magnuson V L, Ally D S, Nylund S J, Karanjawala Z E, Rayman J B, Knapp J I, Lowe A L, Ghosh S, Collins F S (1996). Substrate nucleotide-determined non-templated addition of adenine by Taq DNA polymerase: implications for PCR-based genotyping and cloning. Biotechniques 4:700-9.

Makarova O, Kamberov E, Margolis B (2000). Generation of deletion and point mutations with one primer in a single cloning step. Biotechniques 5:970-2.

Mills D A, McKay L L, Dunny G M (1996). Splicing of a group II intron involved in the conjugative transfer of pRS01 in Lactococci. J Bacteriol 178: 3531-38.

Mohr G, Ghanem E, Lambowitz A M (2010). Mechanisms used for genomic proliferation by thermophilic group II introns. PLoS Biol 8:e1000391.

Moretz, S. E. & Lampson, B. C. (2010). A group IIC-type intron interrupts the rRNA methylase gene of *Geobacillus stearothermophilus* strain 10. J Bacteriol 192: 5245-5248.

Oz-Gleenberg I, Herschhorn A, Hizi A (2011). Reverse transcriptases can clamp together nucleic acids strands with two complementary bases at their 3'-termini for initiating DNA synthesis. Nucleic Acids Res 3:1042-53.

Park W, Li J, Song R, Messing J, Chen X (2002). CARPEL FACTORY, a Dicer homolog, and HEN1, a novel protein, act in microRNA metabolism in *Arabidopsis thaliana*. Curr Biol 12:1484-95.

Patel P H, Preston B D (1994). Marked infidelity of human immunodeficiency virus type 1 reverse transcriptase at RNA and DNA template ends. Proc Natl Acad Sci USA 91:549-53.

Peliska J A, Benkovic S J (1992). Mechanism of DNA strand transfer reactions catalyzed by HIV-1 reverse transcriptase. Science 258:1112-8.

Polidoros A N, Pasentsis K, Tsaftaris A S (2006). Rolling circle amplification-RACE: a method for simultaneous isolation of 5' and 3' cDNA ends from amplified cDNA templates. Biotechniques 41:35-42.

Saldanha R, Chen B, Wank H, Matsuura M, Edwards J, Lambowitz A M (1999). RNA and protein catalysis in group II intron splicing and mobility reactions using purified components. Biochemistry 38:9069-83.

Sambrook J, Fritsch E F, and Maniatis T. (1989) Molecular Cloning: A Laboratory Manual. Cold Spring Harbor Laboratory Press, NY.

Simon D & Zimmerly S (2008). A diversity of uncharacterized retroelements in bacteria. Nucleic Acids Res 36:7219-7229.

Smith D, Zhong J, Matsuura M, Lambowitz A M, Belfort M (2005). Recruitment of host functions suggests a repair pathway for late steps in group II intron retrohoming. Genes Dev 19:2477-87.

Studier F W (2005). Protein production by auto-induction in high density shaking cultures. Protein Expr Purif 1:207-34.

Vellore J, Moretz S E & Lampson BC (2004). A group II intron-type open reading frame from the thermophile *Bacillus* (*Geobacillus*) *stearothermophilus* encodes a heat-stable reverse transcriptase. Appl Environ Microbiol 70:7140-7147 (2004).

Xiong Y, Eickbush T H (1990). Origin and evolution of retroelements based upon their reverse transcriptase sequences. EMBO J 9:3353-62.

Zhang C & Darnell R B (2011). Mapping in vivo protein-RNA interactions at single-nucleotide resolution from HITS-CLIP data. Nat Biotechnol 29: 607-614.

Zhong J, Lambowitz A M (2003). Group II intron mobility using nascent strands at DNA replication forks to prime reverse transcription. EMBO J 22:4555-65.

Zhu Y Y, Machleder E M, Chenchik A, Li R, Siebert P D (2001). Reverse transcriptase template switching: a SMART approach for full-length cDNA library construction. Biotechniques 30: 892-97.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing a DNA copy of a target polynucleotide using template switching, comprising:
   mixing at least one double stranded template/primer substrate, consisting of a DNA primer oligonucleotide annealed with a complementary oligonucleotide template strand, with at least one target polynucleotide in a reaction medium, and
   adding a suitable amount of a non-retroviral reverse transcriptase to the reaction medium to extend the DNA primer oligonucleotide from its 3' end to provide a DNA copy polynucleotide that includes a complementary target DNA polynucleotide that is synthesized using the target polynucleotide as a template
   wherein the double stranded template/primer substrate has a blunt end wherein the 3' end of the DNA primer oligonucleotide is directly aligned with the 5' end of the complementary oligonucleotide template strand, or an overhanging end wherein the 3' end of the DNA primer oligonucleotide extends 1 nucleotide beyond the 5' end of the complementary oligonucleotide template strand.

2. The method of claim 1, wherein the target polynucleotide consists of RNA.

3. The method of claim 2, wherein the target polynucleotide is a miRNA.

4. The method of claim 1, wherein the target polynucleotide consists of DNA.

5. The method of claim 1, wherein the complementary oligonucleotide template strand consists of RNA.

6. The method of claim 1, wherein the complementary oligonucleotide template strand consist of DNA.

7. The method of claim 1, wherein the double stranded template/primer substrate has an overhanging end and wherein a plurality of different double stranded template/primer substrates are used that have overhanging ends consisting of from 2-4 different nucleotides.

8. The method of claim 1, wherein the DNA primer oligonucleotide has an overhanging end and wherein the nucleotide at the 3' end of the target polynucleotide is complementary to the nucleotide at the 3' end of the DNA primer oligonucleotide.

9. The method of claim 1, wherein the non-retroviral reverse transcriptase adds 1-15 additional non-complementary nucleotides at the 3' end of the DNA primer oligonucleotide before copying the target polynucleotide to synthesize the DNA copy polynucleotide.

10. The method of claim 9, wherein the non-retroviral reverse transcriptase adds only a single additional non-complementary nucleotide.

11. The method of claim 1, wherein the 3' end of the complementary oligonucleotide template strand is terminated by a blocking agent.

12. The method of claim 1, wherein the non-retroviral reverse transcriptase is a group II intron reverse transcriptase.

13. The method of claim 1, wherein a cloning library of a plurality of DNA copy polynucleotides is prepared by using a plurality of different target polynucleotides.

14. The method of claim 1, further comprising the step of circularizing the DNA copy polynucleotide.

15. A method of preparing a DNA copy of a target polynucleotide using template switching, comprising:
- mixing at least one double stranded template/primer substrate, consisting of a DNA primer oligonucleotide annealed with a complementary oligonucleotide template strand, with at least one target polynucleotide in a reaction medium, and
- adding a suitable amount of a group II intron reverse transcriptase to the reaction medium to extend the DNA primer oligonucleotide from its 3' end to provide a DNA copy polynucleotide that includes a complementary target DNA polynucleotide that is synthesized using the target polynucleotide as a template.

16. The method of claim 15, wherein the target polynucleotide consists of RNA.

17. The method of claim 16, wherein the target polynucleotide is a miRNA.

18. The method of claim 15, wherein the target polynucleotide consists of DNA.

19. The method of claim 15, wherein the complementary oligonucleotide template strand consists of RNA.

20. The method of claim 15, wherein the complementary oligonucleotide template strand consist of DNA.

21. The method of claim 15, wherein the double stranded template/primer substrate has a blunt end wherein the 3' end of the DNA primer oligonucleotide is directly aligned with the 5' end of the complementary oligonucleotide template strand.

22. The method of claim 15, wherein the double stranded template/primer substrate has an overhanging end wherein the 3' end of the DNA primer oligonucleotide extends 1 nucleotide beyond the 5' end of the complementary oligonucleotide template strand.

23. The method of claim 22, wherein a plurality of different double stranded template/primer substrates are used that have overhanging ends consisting of from 2-4 different nucleotides.

24. The method of claim 22, wherein the nucleotide at the 3' end of the target polynucleotide is complementary to the nucleotide at the 3' end of the DNA primer oligonucleotide.

25. The method of claim 15, wherein the reverse transcriptase adds 1-15 additional non-complementary nucleotides at the 3' end of the DNA primer oligonucleotide before copying the target polynucleotide to synthesize the DNA copy polynucleotide.

26. The method of claim 25, wherein the reverse transcriptase adds only a single additional non-complementary nucleotide.

27. The method of claim 15, wherein the 3' end of the complementary oligonucleotide template strand is terminated by a blocking agent.

28. The method of claim 15, wherein a cloning library of a plurality of DNA copy polynucleotides is prepared by using a plurality of different target polynucleotides.

29. The method of claim 15, further comprising the step of circularizing the DNA copy polynucleotide.

30. A method of adding additional nucleotides to a DNA primer oligonucleotide, comprising adding a suitable amount of a non-retroviral reverse transcriptase to a reaction medium comprising a double stranded template/primer substrate consisting of a DNA primer oligonucleotide annealed with a complementary oligonucleotide template strand, wherein the non-retroviral reverse transcriptase adds 1-15 additional non-complementary nucleotides at the 3' end of the DNA primer oligonucleotide.

31. The method of claim 30, wherein the non-retroviral reverse transcriptase is a group II intron reverse transcriptase.

32. The method of claim 30, wherein 1-6 additional non-complementary nucleotides are added.

33. The method of claim 30, wherein a single non-complementary nucleotide is added.

* * * * *

SEQUENCE LISTING

```
<160> NUMBER OF SEQ ID NOS: 137

<210> SEQ ID NO 1
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gugcgcccag auagggguguu aagucaagua                                        30

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacaccctat ctgggcgcac                                                    20

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 3

Thr Val Asp Glu Ala Leu Lys Asp Ala Gln Thr Asn Ser Ser Ser Asn
1               5                   10                  15

Asn Asn Asn Asn Asn Asn Asn Asn Asn Leu Glu Asn Leu Tyr Phe Gln
            20                  25                  30

Gly

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 4

Thr Val Asp Ala Ala Leu Ala Ala Ala Gln Thr Asn Ala Ala Ala Ala
1               5                   10                  15

Ala

<210> SEQ ID NO 5
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
```
cgccuuggcc guacagcagc cucucuaugg gcagucggug au                42

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 6
atcaccgact gcccatagag agccugctgt a                            31

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other

<400> SEQUENCE: 7
nncgcuucag agagaaaucn n                                       21

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccactacgcc tccgctttcc tctctatggg cagtcggtga t                 41

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgccccggg ttcctcattc tct                                     23

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgctgtacg gccaaggcg                                          19

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gugcgcccag auagggguguu cucguuggca auggugucca acuugugcug ccagugcucg    60

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 12
cgagcactgg cagcacaagu tggacaccat tgccaacgag aacac    45

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgtgattgca acccacgtcg atcgtgaaca catccataac    40

<210> SEQ ID NO 14
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugugauugca acccacgucg aucgugaaca cauccauaac    40

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
catatcattt ttaattctac gaatctttat actggcaaac    40

<210> SEQ ID NO 16
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cauaucauuu uuaauucuac gaaucuuuau acuggcaaac          40

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 17
catctggcgg ctgttctcgu tggacaccat tgccaacgag gtttgccagt ataaagattc    60
gtagaattaa          70

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cttgtgctgc cagtgctcg          19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tggacaccat tgccaacgag          20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgagaacagc cgccagatg          19

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtaaaacgac ggccagt          17

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 22
caggaaacag ctatgac                                                 17

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaacagct atgaccatg                                               19

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 24
atcaccgact gcccatagag aggcugcugu a                                 31

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cctatctggg cgccacgtta                                              20

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other

<400> SEQUENCE: 26
nncgcuucag agagaaaucn n                                            21

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
```
cgccuuggcc guaca                                              15

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (20)..(21)
<223> OTHER INFORMATION: a, c, t, g, unknown or other

<400> SEQUENCE: 28
nngatttctc tctgaagcgn n                                       21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaggcgattt ctctctgaag                                         20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aaggcgatga tttctctctg aag                                     23

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaggcgggct gctagctctg aagcgct                                 27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aaggcgccga tttctctctg aagcgct                                 27

<210> SEQ ID NO 33
<211> LENGTH: 27

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaggcgaaga tttctctctg aagcgct                                           27

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaggcgcgga tttctctctg aagcgcca                                          28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aaggcgatga tttctctctg aagcggca                                          28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaggcggcga tttctctctg aagcgtgg                                          28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaggcgatga tttctctctg tgttagga                                          28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaggcgcgat ttctctctga agcggcaa                                          28

<210> SEQ ID NO 39
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 39
aaggcgatga tttctctctg aagcggtga                                       29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: a, c, t, g, unknown or other

<400> SEQUENCE: 40
aaggcgagga tttctctctg aagcgntga                                       29

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
aaggcgatga tttctctctg aagcgctga                                       29

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaggcgcgga tttctctctg aagcgacaa                                       29

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aaggcgcgga tttctctctg aagcgacaa                                       29

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaggcggtga tttctctctg aagcgtgga                                       29
```

```
<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaggcgacga tttctatctg aagcgagac                                      29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aaggcggaga tttctctctg aagcgccaa                                      29

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaggcgctga tttctctctg aagcgccaag                                     30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaggcgaaga tttctctctg aagcgtcaag                                     30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
aaggcgcgga tttctctctg aagcgccaga                                     30

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aaggcgatga tttctctctg aagcgccagg at                                  32

<210> SEQ ID NO 51
```

```
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other
<220> FEATURE:
<221> NAME/KEY: modified_base
<222> LOCATION: (20)..(20)
<223> OTHER INFORMATION: a, c, t, g, unknown or other

<400> SEQUENCE: 51
aaggcggtga tttntnnntn aagcgcaaac ccctcaaa                              38

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aaggcgctga tttctctctg aagcgccaac cccctca                               38

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
aaggcgacga tttctctctg aagcgccagc aggacgttca tg                         42

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
taacgugcgc ccagauagg                                                   19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cctatctggg cgcacgtta                                                   19
```

```
<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctatctggg cgca                                                           14

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cctatctggg cgcac                                                          15

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cctatctggg cgcacaa                                                        17

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cctatctggg cgcacaaa                                                       18

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctatctggg cgcacaagtt a                                                   21

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cctatctggg cgcacgtta                                                      19

<210> SEQ ID NO 62
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cctatctggg cgcacagtta                                               20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cctatctggg cgcacaagtt a                                             21

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uaacgugcgc ccagauagg                                                19

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tctatctggg cgcac                                                    15

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctatctggg cgcacat                                                  17

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cctatctggg cgcacaga                                                 18

<210> SEQ ID NO 68
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cctatctggg ctcacaaaa                                                19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cctatctggg cgcacatta                                                19

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cctatctggg cgcacgatta                                               20

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cctatctggg cgcacctta                                                19

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cctatctggg cgcactta                                                 18

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cctatctggg cgcacatta                                                19

<210> SEQ ID NO 74
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 74
cctatctgag cgcacaagtt a                                            21

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
catatcattt                                                         10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aaatgatatg                                                         10

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aaatgatatg ccca                                                    14

<210> SEQ ID NO 78
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaatgatatg cccaaa                                                  16

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aaatgatatg ccccaa                                                  16

<210> SEQ ID NO 80
<211> LENGTH: 16
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 80
aaatgatatg cccgaa                                                      16

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaatgatatg cccaaaa                                                     17

<210> SEQ ID NO 82
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aaatgatatg cccccaa                                                     17

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aaatgatatg ccccccc                                                     17

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aaatgatatg ccccgaa                                                     17

<210> SEQ ID NO 85
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaaatgatat gccca                                                       15

<210> SEQ ID NO 86
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 86
aaaatgatat gcccg                                                        15

<210> SEQ ID NO 87
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aaaccauauc auuu                                                         14

<210> SEQ ID NO 88
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
aaatgatatg gttt                                                         14

<210> SEQ ID NO 89
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tatgcccaaa                                                              10

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aaatgatatg cccgggttt                                                    19

<210> SEQ ID NO 91
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tatgcccgaa                                                              10

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 92
aaatgatatg ccccggttt                                                    19

<210> SEQ ID NO 93
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tatgcccggg ttt                                                          13

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aaatgatatg cccggggttt                                                   20

<210> SEQ ID NO 95
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tatgcccggg gttt                                                         14

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aaatgatatg cccaggggtt t                                                 21

<210> SEQ ID NO 97
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tatgccccag                                                              10

<210> SEQ ID NO 98
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 98
tatgcccctg gttt                                                        14

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaatgatatg cccccccgttt                                                 20

<210> SEQ ID NO 100
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tatgcccagg ttt                                                         13

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaatgatatg cccgaggggg ttt                                              23

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tatgcccact ggttt                                                       15

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaatgatatg cccctgggtt t                                                21

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 104
tatgcccagg ggttt                                                    15

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaatgatatg ccccactggt tt                                            22

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tatgcccaaa a                                                        11

<210> SEQ ID NO 107
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tatgccccag ggttt                                                    15

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aaatgatatg ccccggttt                                                19

<210> SEQ ID NO 109
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tatgcccaat                                                          10

<210> SEQ ID NO 110
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
```
tatgccctgg gttt                                                14

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aaatgatatg cccaggggt tt                                        22

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tatgcccaaa a                                                   11

<210> SEQ ID NO 113
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tatgccccag gttt                                                14

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
aaatgatatg cccctgggtt t                                        21

<210> SEQ ID NO 115
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tatgcccggt tt                                                  12

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
aaatgatatg cccaaacgca g                                              21
```

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
aggatttctc tctgaagcgc t                                              21
```

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
acgatttctc tctgaagcgc t                                              21
```

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
aggatttctc tctgaagcgc c                                              21
```

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
aagatttctc tctgaagcgc t                                              21
```

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

```
acgatttctc tctgaagcgc c                                              21
```

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

```
atgatttctc tctgaagcgc t                                              21
```

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aggatttctc tctgaagcgc a                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
acgatttctc tctgaagcga t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
acgatttctc tctgaagcgt a                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
acgatttctc tctgaagcgt t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atgatttctc tctgaagcgc c                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
aggatttctc tctgaagcgt c                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aggatttctc tctgaagcgt t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
atgatttctc tctgaagcgc a                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aggatttctc tctgaagcga c                                              21

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aggatttctc tctgaagcgc ca                                             22

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acgatttctc tctgaagcgc ca                                             22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atgatttctc tctgaagcgc ca                                             22

```
<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atgatttctc tctgaagcga ca                                              22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
aggatttctc tctgaagcga ca                                              22

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, u, g, unknown or other

<400> SEQUENCE: 137
gccgcuucag agagaaaucg n                                               21
```